US007678779B2

(12) United States Patent
Cassatt et al.

(10) Patent No.: US 7,678,779 B2
(45) Date of Patent: *Mar. 16, 2010

(54) METHODS FOR THE ADMINISTRATION OF AMIFOSTINE AND RELATED COMPOUNDS

(75) Inventors: David Cassatt, Frederick, MD (US); Christine A. Fazenbaker, Boonsboro, MD (US)

(73) Assignee: MedImmune, LLC, Gaithersburg, MD (US)

( * ) Notice: Subject to any disclaimer, the term of this patent is extended or adjusted under 35 U.S.C. 154(b) by 23 days.

This patent is subject to a terminal disclaimer.

(21) Appl. No.: 12/070,859

(22) Filed: Feb. 20, 2008

(65) Prior Publication Data

US 2008/0207566 A1    Aug. 28, 2008

Related U.S. Application Data

(60) Continuation of application No. 11/351,166, filed on Feb. 8, 2006, now Pat. No. 7,368,440, which is a division of application No. 10/140,108, filed on May 8, 2002, now Pat. No. 7,053,072.

(60) Provisional application No. 60/290,024, filed on May 11, 2001.

(51) Int. Cl.
*A01N 31/00* (2006.01)
*A01N 33/02* (2006.01)
*A01N 33/08* (2006.01)
*A01N 43/78* (2006.01)
*A01N 57/00* (2006.01)

(52) U.S. Cl. ................ 514/114; 514/365; 514/649; 514/665; 514/706

(58) Field of Classification Search .............. None
See application file for complete search history.

(56) References Cited

U.S. PATENT DOCUMENTS

| 3,892,824 | A | 7/1975 | Piper et al. ............ 558/166 |
| 4,656,034 | A | 4/1987 | Sarnoff ................ 424/94 |
| 5,091,180 | A | 2/1992 | Walker et al. ........... 424/944 |
| 5,167,947 | A | 12/1992 | Geary ................. 424/11 |
| 5,217,964 | A | 6/1993 | Edwards et al. .......... 514/104 |
| 5,424,471 | A | 6/1995 | Kennedy et al. ......... 558/146 |
| 5,434,145 | A | 7/1995 | Edwards et al. .......... 514/108 |
| 5,466,678 | A | 11/1995 | Kawabata et al. ......... 514/46 |
| 5,488,042 | A | 1/1996 | Grdina ................ 514/114 |
| 5,567,686 | A | 10/1996 | Grdina ................. 514/43 |
| 5,591,731 | A | 1/1997 | Kennedy et al. .......... 514/114 |
| 5,605,931 | A | 2/1997 | Hanson ................. 514/530 |
| 5,618,823 | A | 4/1997 | Cavelletti et al. ......... 514/283 |
| 5,807,744 | A | 9/1998 | Berneman et al. ......... 435/372 |
| 5,846,958 | A | 12/1998 | Capizzi et al. ........... 514/114 |
| 5,869,338 | A | 2/1999 | Grdina ................ 435/375 |
| 5,891,856 | A | 4/1999 | Grdnia ................. 514/43 |
| 5,972,986 | A | 10/1999 | Seibert et al. ............ 514/406 |
| 5,994,409 | A | 11/1999 | Stogniew et al. .......... 514/665 |
| 6,028,114 | A | 2/2000 | Quash ................. 514/665 |
| 6,051,563 | A | 4/2000 | Stogniew et al. .......... 514/114 |
| 6,054,622 | A | 4/2000 | Zhang et al. ............ 568/62 |
| 6,066,668 | A | 5/2000 | Hausheer et al. .......... 514/492 |
| 6,075,053 | A | 6/2000 | Hausheer .............. 514/578 |
| 6,114,394 | A | 9/2000 | Edwards et al. .......... 514/646 |
| 6,127,351 | A | 10/2000 | Stogniew et al. .......... 514/114 |
| 6,218,377 | B1 | 4/2001 | Stogniew et al. .......... 514/114 |
| 6,489,312 | B1 | 12/2002 | Stogniew ............... 514/109 |
| 6,573,253 | B2 * | 6/2003 | Stogniew ............... 514/114 |
| 7,053,072 | B2 * | 5/2006 | Cassatt et al. ............ 514/114 |
| 7,368,440 | B2 * | 5/2008 | Cassatt et al. ............ 514/114 |

FOREIGN PATENT DOCUMENTS

| WO | WO 89/05637 | 6/1989 |
| WO | WO 89/07942 | 9/1989 |
| WO | WO 90/14007 | 11/1990 |
| WO | WO 94/22307 | 10/1994 |
| WO | WO 96/25045 | 8/1996 |
| WO | WO 97/11666 | 4/1997 |
| WO | WO 98/34622 | 8/1998 |
| WO | WO 99/30705 | 6/1999 |
| WO | WO 00/56299 | 9/2000 |
| WO | WO 02/062350 | 8/2002 |

OTHER PUBLICATIONS

Capizzi, "The Preclinical Basis for Broad-Spectrum Selective Cytoprotection of Normal Tissues Froqm Cytotoxic Therapies by Amifostine (Ethylol™).," European Journal of Cancer, 37A(Suppl. 4), S5-S16 (1996).*
Korst et al., "Pharmacokinetics of Amifostine and its Metabolites in Patients," European Journal of Cancer, 33(9), 1425-1429 (Aug. 1997).*
Betticher et al., 1995, "Carboplatin combined with amifostine, a bone marrow protectant, in the treatment of non-small-cell lung cancer: a randomised phase II study," Br. J. Cancer 5: 1551-1555.
Bohuslavizki, K.H., et al., May 1997, "Protective Effect of Amifostine on Salivary Glands of Rabbits Treated With High Dose of Iodine-131," Scientific Abstracts of the 44th Annual Meeting of the Society of Nuclear Medicine, San Antonio, Texas, Jun. 1-5, 1997, No. 950; Journal of Nuclear Medicine 38(5) May 1997 Suppl.
Bohuslavizki et al., 1997, "Protection of salivary glands by amifostine in patients treated with high dose radioiodine", Eu. Jour. Cancer 33: S17.
Boven et al., 2002, "BNP7787, a novel protector against platinum-related toxicities, does not affect the efficacy of cisplatin or carboplatine in human tumour xenografts", Eur. J. Cancer 38: 1148-1156.
Brizel et al., 2000, "Phase III Randomized Trial of Amifostine as a Radioprotector in Head and Neck Cancer," Journal of Clinical Oncology 18(19): 3339-3345.

(Continued)

*Primary Examiner*—Lawrence E Crane
(74) *Attorney, Agent, or Firm*—Jones Day

(57) ABSTRACT

The present invention provides methods of administering amifostine, WR-1065, or a combination thereof, to patients receiving radiation therapy or chemotherapy in a manner that significantly reduces or decreases the adverse or undesirable side-effects of the compounds as compared with conventional intravenous administration.

30 Claims, 11 Drawing Sheets

OTHER PUBLICATIONS

Buntzel et al., 1998, "Selective cytoprotection with amifostine in concurrent radiochemotherapy for head and neck cancer", Ann Oncol 9: 505-509.

Buntzel, J. et al., 1998, "Radiochemotherapy With Amifostine Cytoprotection For Head and Neck Cancer" Support Care Cancer 6:155-160.

Buntzel, J. , 1998, "Intensification of Radiochemistry With Amifostine in Head and Neck Cancer", P Ann M Am Soc. vol. 17 Abstract No. 1555.

Buntzel J. et al., 1997 "Selective cytoprotection with amifostine: A new strategy in supportive care of head and neck malignancies", Oto-Rhino Laryngologia Nova 7(5-6): 276-280.

Buntzel et al., 1996, "Ethyol® (Amifostine) Provides Multilineage Hematoprotection and Protection Against Non-Hematologic Toxicities Induced by Radiochemotherapy (RCT) of Head and Neck Cancer," Blood 88(Supp. 1): 1781.

Buntzel et al., 1997, "Amifostine in Simultaneous Radiochemotherapy of Head and Neck Cancer", Oto-Rhino-Laryngologia Nova 7(4): 204-210.

Buntzel et al., 1997, "Intensive Radiochemotherapy (RCT) with Amifostine (A) in Head and Neck (H & N) Cancer", Eur. J. Cancer 33(Suppl. 8): S17-S18.

Busch, B. et al., 1997, "Cytoprotection With Amifostine in Recurrent Head and Neck Cancer," Abstract, No. 1418, Proceedings of ASCO, vol. 16. 397a.

Caldwell, R.W. and Heiffer, M.H., 1975, "Acute Cardiovascular and Autonomic Effects of WR-2721: A Radioprotective Compound", Radiation Research 62:62-69.

Constine, et al. Aug. 1986, "Protection by WR-2721 of Human Bone Marrow Function Following Irradiation," Int. J. Radiation Oncology Biol. Phys., 12(8):1505-1508.

Culy et al., 2001, "Amifostine: An Update on its clinical status as a cytoprotectant in patients with cancer receiving chemotherapy or radiotherapy and its potential therapeutic application in myelodyplastic syndrome", Drugs 61(5): 641-684.

Dorr et al., 1995, "Selective Cardioprotection of Rat Heart Myocytes Exposed to DNA Intercalating Agents Using Amifostine (AMI) and its Dephosphorylated Metabolite, WR-1065," Eur. J. Cancer 31A(Supp. 5): S123(579.

Doz et al., 1991, "Experimental Basis for Increasing the Therapeutic Index of Carboplatin in Brain Tumor Therapy by Pretreatment With WR-Compounds", Cancer Chemother. Pharmacol. 28:308.

Foster-Nora et al., 1997, "Amifostine for protection from antineoplastic drug toxicity", Am. Jour. Health-system Pharm. 54(7): 787-800.

Grdina et al., 1985, "The Radioprotector WR-1065 Reduces Radiation-Induced Mutations of the Hypoxanthine-Guanine Phosphoribosye Transferase Locus in V79 Cells", Carcinogenesis (London) 6:929-931.

Grdina, J. & Sigdestad, C., 1989, "Radiation Protectors: The Unexpected Benefits", Drug Metab. Rev. 20(1):13-42.

Hensely et al., 1999, American Society of Clinical Oncology Clinical Practice Guidelines for the Use of Chemotherapy and Radiochemistry Protectants, 17(10): 3333-3355.

Kemp et al., 1996, "Amifostine Pretreatment of Protection Against Cyclophosamide-induced and Cisplatin-induced Toxicities: Results of a Randomized Control Trial in Patient with Advanced Ovarian Cancer", J. Clin. Oncology 14:2101-2112.

Koukourakis et al., *European Journal of Cancer* 35:S98 (1999) Abstract.

Koukourakis et al., *Journal of Clinical Oncology* 18 (11):2226-2233(2000).

McDonald, S. et al., 1995, "Amifostine Preserves The Salivery Gland Function During Irradiation of the Head and Neck," ECCO 8 Paris-Oct. 29-Nov. 2, 1995, The European Journal of Cancer, vol. 31A, Supplement 5, Poster 415.

Phillips and Wasserman, 1984, "Promise of Radiosensitizers and Radioprotectors in the Treatment of Human Cancer," Cancer Treat. Rep. 68:291-302.

Ravo et al., *European Journal of Cancer* 35:S102-103 (1999) Abstract.

Savoye, C. et al., 1997, "Thiol WR-1065 and disulphide WR-33278, two metabolites of the drug Ethyol (Wr-2721), protect DNA against fast neutron-induced strand breakage", Int. J. Radiat. Biol. 71(2):193-202.

Shaw et al., *Seminars in Oncology* 26(2) suppl 7:34-36 (1999).

Spencer et al., 1995, "Amifostine. A review of its pharmacodynamic and pharmacokinetic properties, and therapeutic potential as a radioprotector and cytotoxic chemoprotector", Drugs 50(6): 1001-1031.

Stogniew et al., *Proceedings of the American Association for Cancer Research Annual Meeting* 40:642 (1999).

Takahashi, I., et al., Jun. 1986, "Clinical Study of the Radioprotective Effects of Amifostine (YM-08310, WR-2721) on Chronic Radiation Injury," Int. J. Radiation Oncology Biol. Phys. 12(6); 935-938.

Tannehill, S.P., et al., Aug. 1996, "Amifostine and Radiation Therapy: Past, Present and Future," Seminars in Oncology 23(No. 4, Suppl. 8): 69-77.

Tannehill, S.P., et al., Aug. 1997, "Effect of Amifostine on Toxicities Associated With Sequential Chemotherapy and Radiation Therapy for Unresectable Non-Small-Cell Lung Cancer: Results of a Phase II Trial," J. of Clinical Oncology 15(8): 2850-2857.

Wasserman, T.H., Oct. 1994, "Radiatherapeutic Studies With Amifostine (Ethyol)," Seminars in Oncology 21(5: suppl. 11): 21-25.

\* cited by examiner

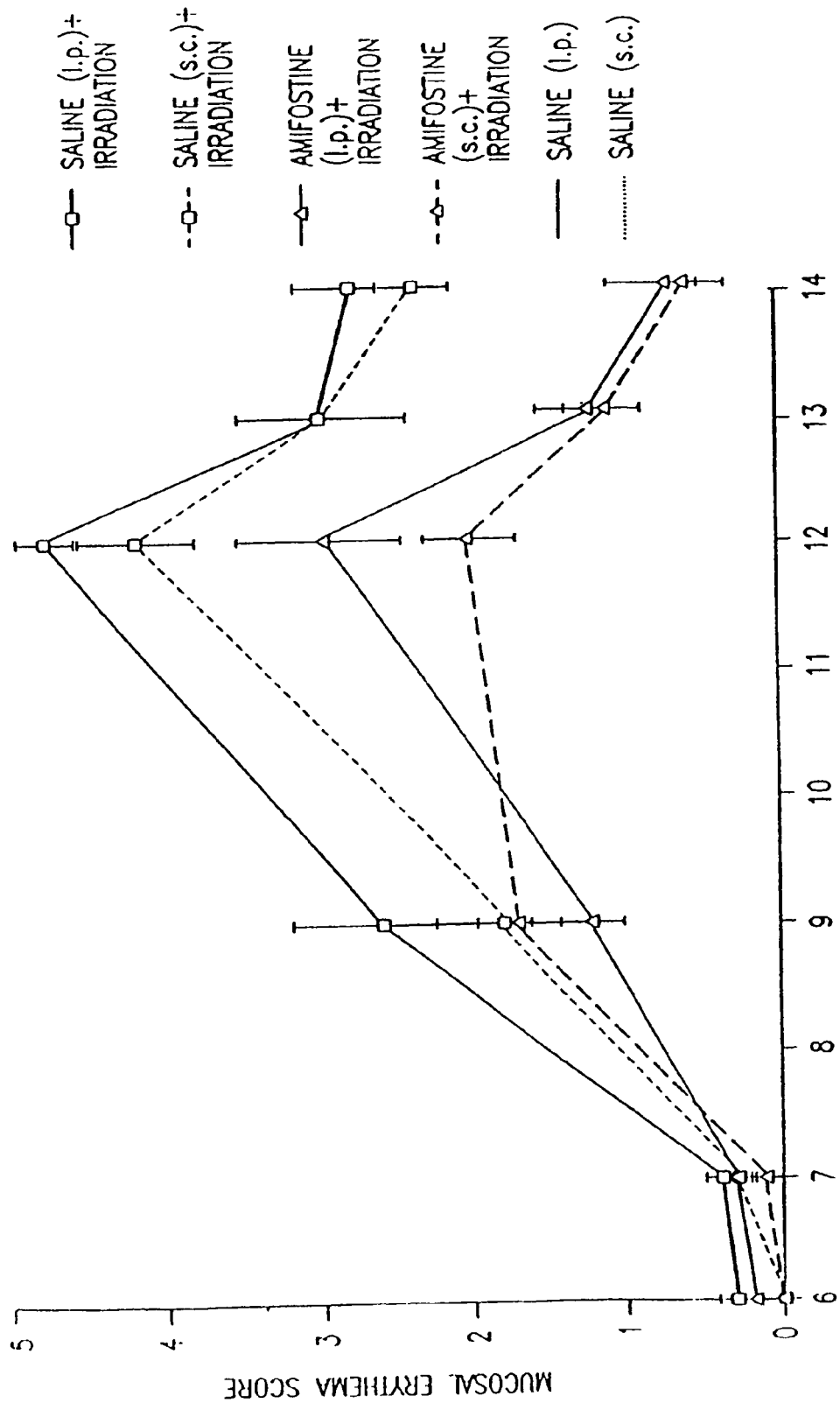

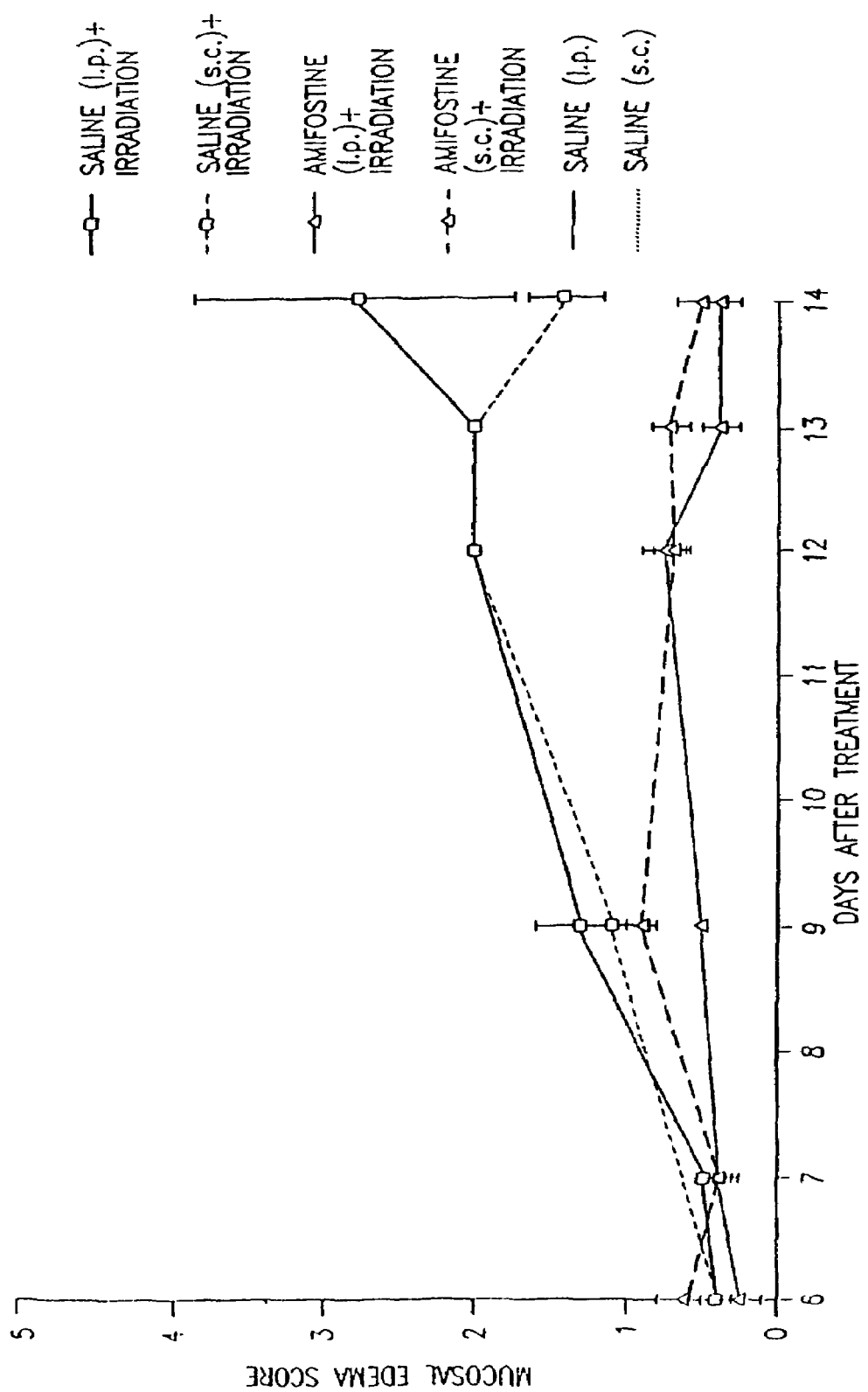

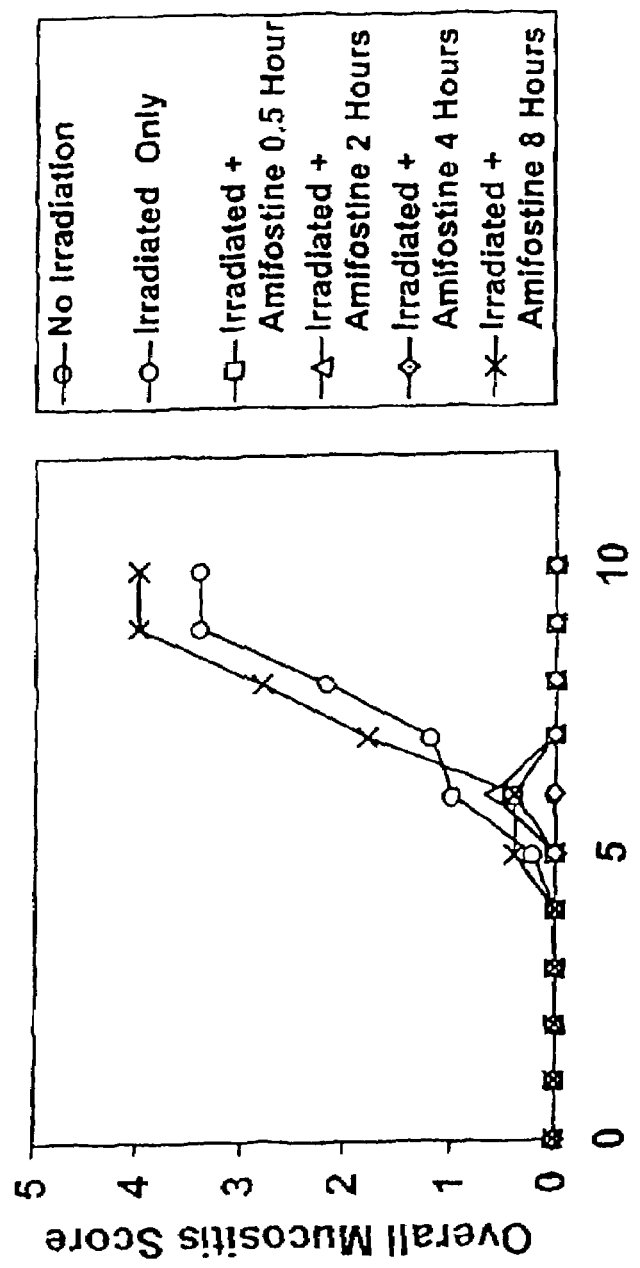

METHODS FOR THE ADMINISTRATION OF AMIFOSTINE AND RELATED COMPOUNDS

This application is a continuation of U.S. patent application Ser. No. 11/351,166, filed Feb. 8, 2006, now U.S. Pat. No. 7,368,440, which is a divisional of U.S. patent application Ser. No. 10/140,108, filed May 8, 2002, now U.S. Pat. No. 7,053,072, which claims the benefit of U.S. Provisional Application No. 60/290,024, filed May 11, 2001, both of which are incorporated herein by reference.

1. INTRODUCTION

The present invention relates to methods of protecting against toxicity associated with cancer therapy, such as ionizing radiation or cancer chemotherapy, which comprises subcutaneously administering amifostine and/or its metabolites to a subject. The invention also relates to methods of treating head and neck cancer and methods of prevention zerostomia or mucositis caused by radiation therapy or cancer chemotherapy.

2. BACKGROUND OF THE INVENTION

Amifostine (also known as WR-2721) has been shown to be useful as a radiation protectant in cancer patients receiving radiation therapy (Constine et al., 1986, "Protection by WR-2721 of Human Bone Marrow Function Following Irradiation" *Int. J. Radia. Oncol. Biol. Phys.* 12:1505-8; Liu et al., 1992, "Use of Radiation with or Without WR-2721 in Advanced Rectal Cancer" *Cancer* 69(11):2820-5; Wadler et al., 1993, "Pilot Trial of Cisplatin, Radiation and WR-2721 in Carcinoma of the Uterine Cervix: A New York Gynecologic Oncology Group Study" *J. Clin. Oncol.* 11(8):1511-6; Büntzel et al., 1996, "Selective Cytoprotection with Amifostine in Simultaneous Radiochemotherapy of Head Neck Cancer" *Ann. Oncol.* 7(Suppl. 5):81(381P)). Amifostine is a prodrug that is dephosphorylated at the tissue site by alkaline phosphatase to the free thiol, which is the active metabolite (also known as WR-1065). Once inside the cell, the active free thiol can protect against the toxicities associated with radiation by acting as a scavenger for oxygen free-radicals that are produced by ionizing radiation (Yuhas, 1977, "On the Potential Application of Radioprotective Drugs in Solid Tumor Radiotherapy," *In: Radiation-Drug Interactions in Cancer Management* pp. 303-52; Yuhas, 1973, "Radiotherapy of Experimental Lung Tumors in the Presence and Absence of a Radioprotective Drug S-2-(3-Aminopropylamino) thylphosphorothioc Acid (WR-2721)" *J. Natl. Cancer Inst.* 50:69-78; Philips et al., 1984, "Promise of Radiosensitizers and Radioprotectors in the Treatment of Human Cancer" *Cancer Treat. Rep.* 68:291-302).

Amifostine's ability to selectively protect normal tissues is based on the differential metabolism and uptake of amifostine into normal tissue versus tumor tissue. Amifostine is rapidly taken up and retained in normal tissues. Differences in capillary and membrane-bound alkaline phosphatase concentration and pH between normal and tumor tissues have been shown to favor the conversion of the pro-drug and uptake of the active form of amifostine, the free thiol, into normal tissues. Coupled with the fact that normal cells concentrate the free thiol at a faster rate than tumors and retain it for longer periods of time, amifostine is able to selectively protect normal tissues against the toxicities associated with radiation without negatively affecting the antitumor response. The marked differences in tissue uptake and retention between normal and tumor tissues produces a temporary state of acquired drug resistance in normal tissues, analogous to that produced by an excess of endogenous glutathione.

For a cytoprotector to be useful in radiation therapy, the compound must be tolerated on a daily basis, up to 4 or 5 days a week for several weeks, prior to the delivery of conventional doses of radiation. McDonald et al. (McDonald, 1994, "Preliminary Results of a Pilot Study Using WR-2721 Before Fractionated Irradiation of Head and Neck to Reduce Salivary Gland Dysfunction" *Int. J. Radiat. Oncol. Biol. Phys.* 29(4): 747-54; McDonald et al., 1995, "Amifostine Preserves the Salivary Gland Function During Irradiation of the Head and Neck" *Eur. J. Cancer* 31a(Supp. 5):415) have conducted a dose-escalation study of amifostine and radiation in patients with head and neck cancer. These results suggest that daily administration of amifostine (200 mg/m$^2$ via a 6-minute intravenous infusion) prior to radiation protects the salivary gland against the toxicities of radiation.

Amifostine has also been shown to stimulate bone marrow growth, and is currently in Phase II clinical trials as a bone marrow stimulant in patients suffering from myelodysplastic syndrome (List et al., 1996, "Amifostine Promotes Multilineage Hematopoiesis in Patients with Myelodysplastic Syndrome (MDS): Results of a Phase I/II Clinical Trial" *Am. J. Hem.* 1 (Abstract); List et al., 1996, "Amifostine Promotes in vitro and in vivo Hematopoiesis in Myelodysplastic Syndromes" *Chem. Found Sympos.* (Abstract); List et al., 1996, "Amifostine Promotes Multilineage Hematopoiesis in Patients with Myelodysplastic Syndrome (MDS): Results of a Phase I/II Clinical Trial," Abstract, 8th Annual Meeting, American Society of Hematology, Orlando, Fla.). In this study, amifostine is being administered via intravenous infusion.

Intravenous administration of amifostine suffers from several serious drawbacks. First, administering compounds intravenously is extremely inconvenient, particularly when a daily dosing schedule for several weeks, or potentially several months in the case of MDS, is necessary, requiring a skilled practitioner to administer the dose. Second, when administered intravenously, patients suffer from dose-dependent undesirable side-effects such as nausea, vomiting, emesis and hypotension, as well as flushing or feeling of warmth, chills or feeling of coldness, dizziness, somnolence, hiccups and sneezing. A decrease in serum calcium concentration is a known pharmacological effect of intravenously administered amifostine. Allergic reactions ranging from mild skin rashes to rigors have also rarely occurred in conjunction with intravenously administered amifostine. At present, there are no known methods, other than co-administering agents such as anti-emetics, of reducing or avoiding these undesirable side effects. Third, there are related costs associated with intravenous administration, including personnel, equipment and medical measures to attenuate side effects.

The human pharmacokinetic profile of amifostine has been investigated in cancer patients following a single intravenous bolus dose (150 mg/kg) (Shaw et al., 1986, "Human Pharmacokinetics of WR-2721" *Int. J. Radiat. Oncol. Biol. Phys.* 12:1501-4), a single 15-minute intravenous infusion (up to 910 mg/m$^2$) (Shaw et al., 1988, "Pharmacokinetics of WR-2721" *Pharmac. Ther.* 39:195-201; Shaw et al., 1994, "Pharmacokinetics of Amifostine in Cancer Patients: Evidence for Saturable Metabolism" *Proc. Amer. Cos. Clin. Oncol.* 13:144; U.S. Bioscience, 1994, "Pharmacokinetics of Single Dose Amifostine (WR-2721; ETHYOL®)" ETH PK 3) and repeated infusions (up to 910 mg/m$^2$ per dose) (U.S. Bioscience, 1994, "Pharmacokinetics of Double Dose Amifostine (WR-2721; ETHYOL®) with Corresponding Measurements of WR-1065 in Plasma and Bone Marrow Cells"

ETH PK 4). These studies showed that amifostine is rapidly cleared from the plasma with a distribution half-life of less than 1 minute and an elimination half-life of approximately 9 minutes. Less than 10% of amifostine remained in the plasma 6 minutes after intravenous administration. No previous human clinical pharmacokinetic studies have been conducted using either orally or subcutaneously administered amifostine.

Tabachnik reported that the oral administration of amifostine reduced sputum viscosity in cystic fibrosis patients (Tabachnik et al., 1980, "Studies on the Reduction of Sputum Viscosity in Cystic Fibrosis Using an Orally Absorbed Protected Thiol." *J. Pharm. Exp. Ther.* 214:246-9; Tabachnik et al., 1982, "Protein Binding of N-2-Mercaptoethyl-13-Diaminopropane via Mixed Disulfide Formation After Oral Administration of WR-2721" *J. Pharm Exp. Ther.* 220:243-6). However, these studies did not demonstrate that this mode of administration reduced adverse side effects commonly associated with intravenously administered amifostine. Furthermore, a study of the pharmacokinetic profile of the administered compounds was not conducted in these patients.

3. SUMMARY OF THE INVENTION

The present invention provides methods of protecting against toxicities associated with cancer therapy, such as ionizing radiation therapy or chemotherapy, in a subject comprising subcutaneously administering to a subject in need thereof an effective amount of amifostine, WR-1065, or a combination thereof at least about 8 hours before the subject is exposed to ionizing radiation. In another embodiment of the invention, amifostine, WR-1065, or a combination thereof is administered between about 8 to about 12 hours before the subject is exposed to the ionizing radiation. The toxicities include, but are not limited to, neurotoxicity, nephrotoxicity, ototoxicity, cardiotoxicity, alopecia, mucositis (acute and/or late), xerostomia (acute and/or late), infertility, pulmonary toxicity, or renal failure. The amount administered can be at least about 500 mg, preferably the amount administered is at least about 500 mg to 1500 mg. Amifostine, WR-1065, or a combination thereof, can be administered as two subcutaneous injections.

In another embodiment of the invention, amifostine, WR-1065, or a combination thereof is administered in the form of a pharmaceutical composition comprising amifostine, WR-1065, or a combination thereof and a pharmaceutically acceptable diluent, i.e. normal saline. The subject is a mammal such as a human.

In yet another embodiment of the invention, the methods can used for treating head and neck cancer with radiation therapy or chemotherapy comprising subcutaneously administering to a subject in need thereof an effective amount of amifostine, WR-1065, or a combination thereof at least about 8 hours before the subject is exposed to ionizing radiation or chemotherapy. When radiation therapy is used, the radiation is administered once daily at a dose of about 1.8 to 2.0 Gy per fraction for a total dose of 50 to 70 Gy, and the amount administered is at least about 500 mg. Preferably, the effective amount administered is at least about 500 mg to 1500 mg. The amount is administered as two subcutaneous injections as a pharmaceutical composition.

In another embodiment of the invention, the methods of the invention can be used for preventing xerostomia or mucositis caused by radiation therapy or chemotherapy comprising subcutaneously administering to a subject in need thereof an effective amount of amifostine, WR-1065, or a combination thereof at least about 8 hours before the subject is exposed to ionizing radiation.

Administering amifostine and/or its metabolites according to the methods of the invention provide therapeutic and prophylactic benefits not provided by conventional intravenous administration, without substantially affecting the efficacy of the applied dose. Methods of the invention can also significantly reduce or decrease adverse or undesirable side effects suffered by patients to whom amifostine and/or WR-1065 is administered. For example, method of the invention can be advantageously used in conjunction with treatment strategies for delivering amifostine and/or its metabolites to patients without inducing the vomiting, nausea, emesis, hypotension or other undesirable side-effects, including but not limited to, flushing or feeling of warmth, chills or feeling of coldness, dizziness, somnolence, hiccups, sneezing, decreased serum calcium levels and allergic reactions that are commonly experienced with conventional intravenous administration.

4. BRIEF DESCRIPTION OF THE DRAWINGS

Figure 4A:
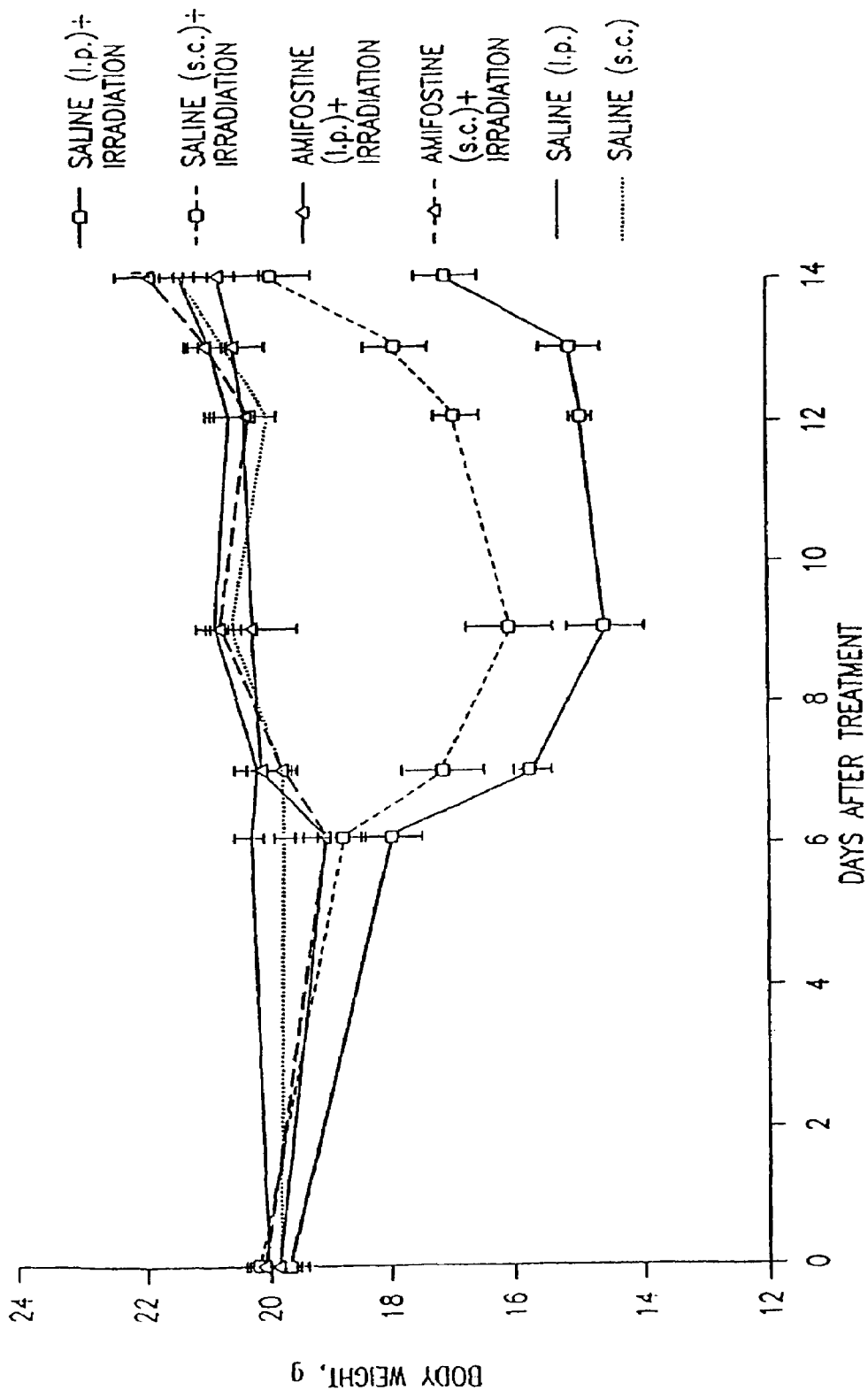
Figure 4B:
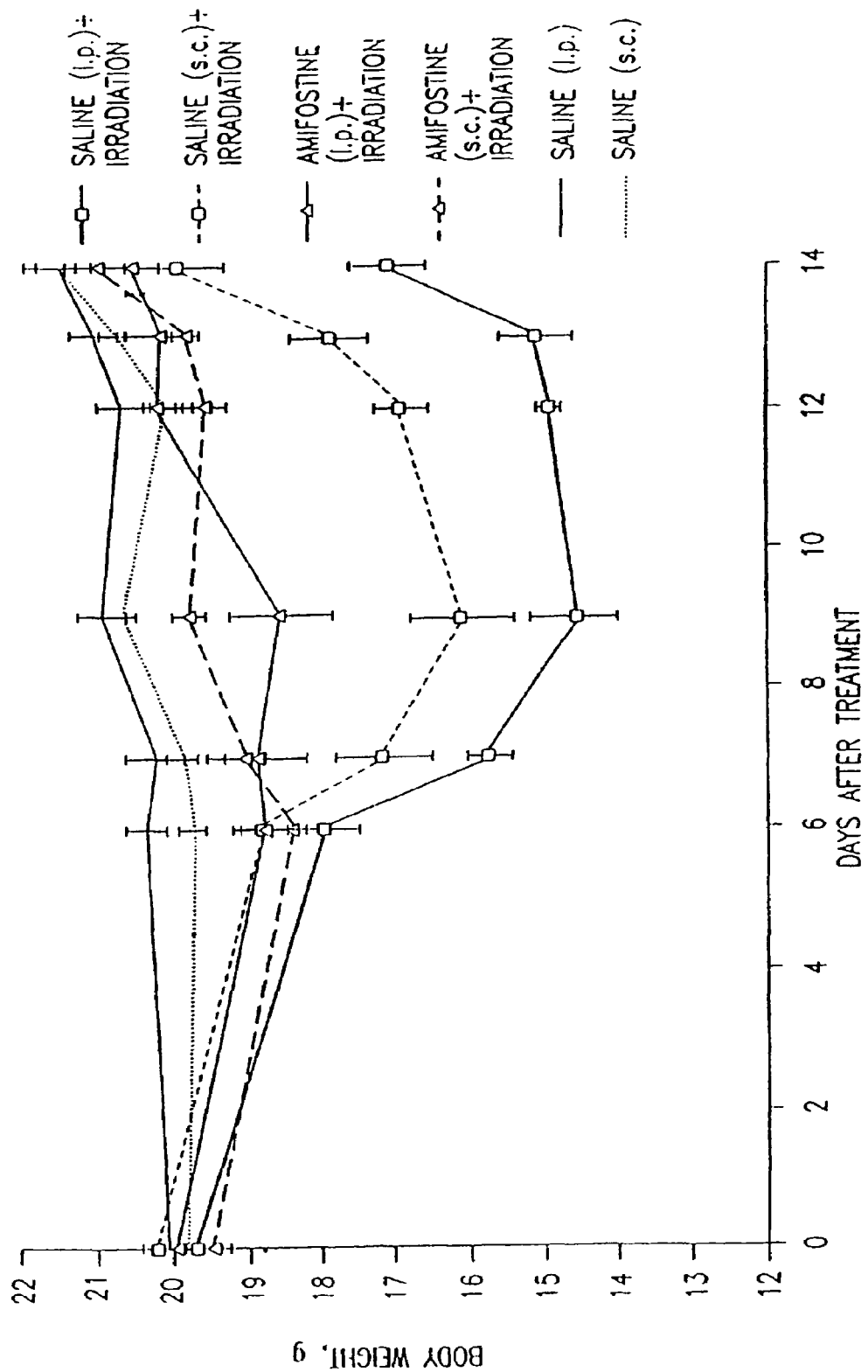

FIGS. 4A and 4B are two graphs of the body weight of animals treated with amifostine or saline and a single dose of irradiation at 16.5 Gy. Amifostine and saline were administered by i.p. and s.c. routes. Control animals received saline without irradiation. Amifostine was dissolved at 500 mg in 9.7 ml of 0.9% NaCl to achieve a final concentration of 50 mg/ml. About 0.1-0.2 ml of amifostine was injected in each animal based on the body weight. Amifostine was administered at a dose of 400 mg/kg body weight (FIG. 4A) and at a dose of 200 mg/kg body weight (FIG. 4B).

Figure 5A:
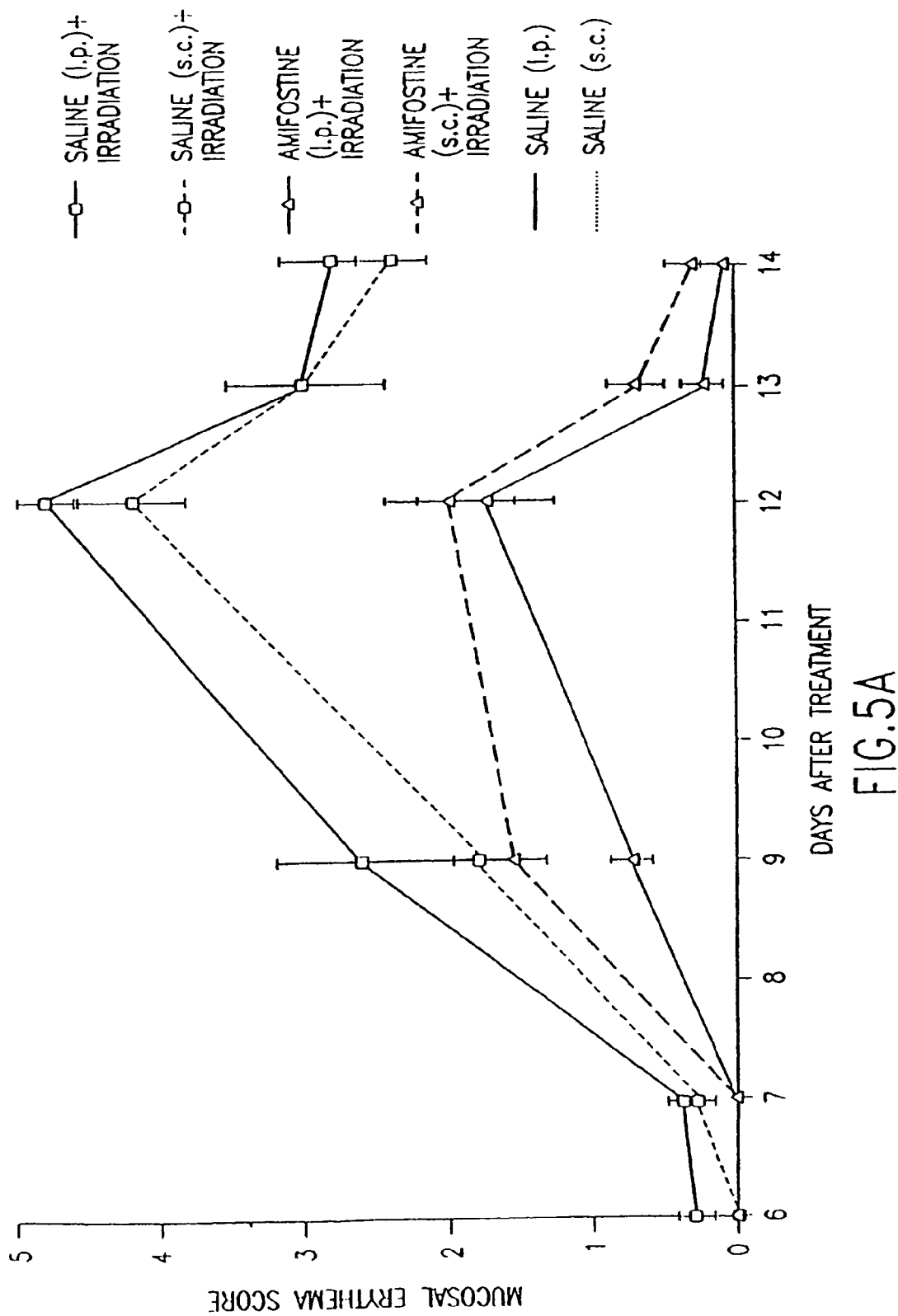

FIGS. 5A and 5B are two graphs of the mucosal erythema scores of animals treated with amifostine or saline and a single dose of irradiation at 16.5 Gy. Amifostine and saline were administered by i.p. and s.c. routes. Control animals received saline without irradiation. Amifostine was dissolved at 500 mg in 9.7 ml of 0.9% NaCl to achieve a final concentration of 50 mg/ml. About 0.1-0.2 ml of amifostine was injected in each animal based on the body weight. Amifostine was administered at a dose of 400 mg/kg body weight (FIG. 5A) and at a dose of 200 mg/kg body weight (FIG. 5B).

Figure 6B:
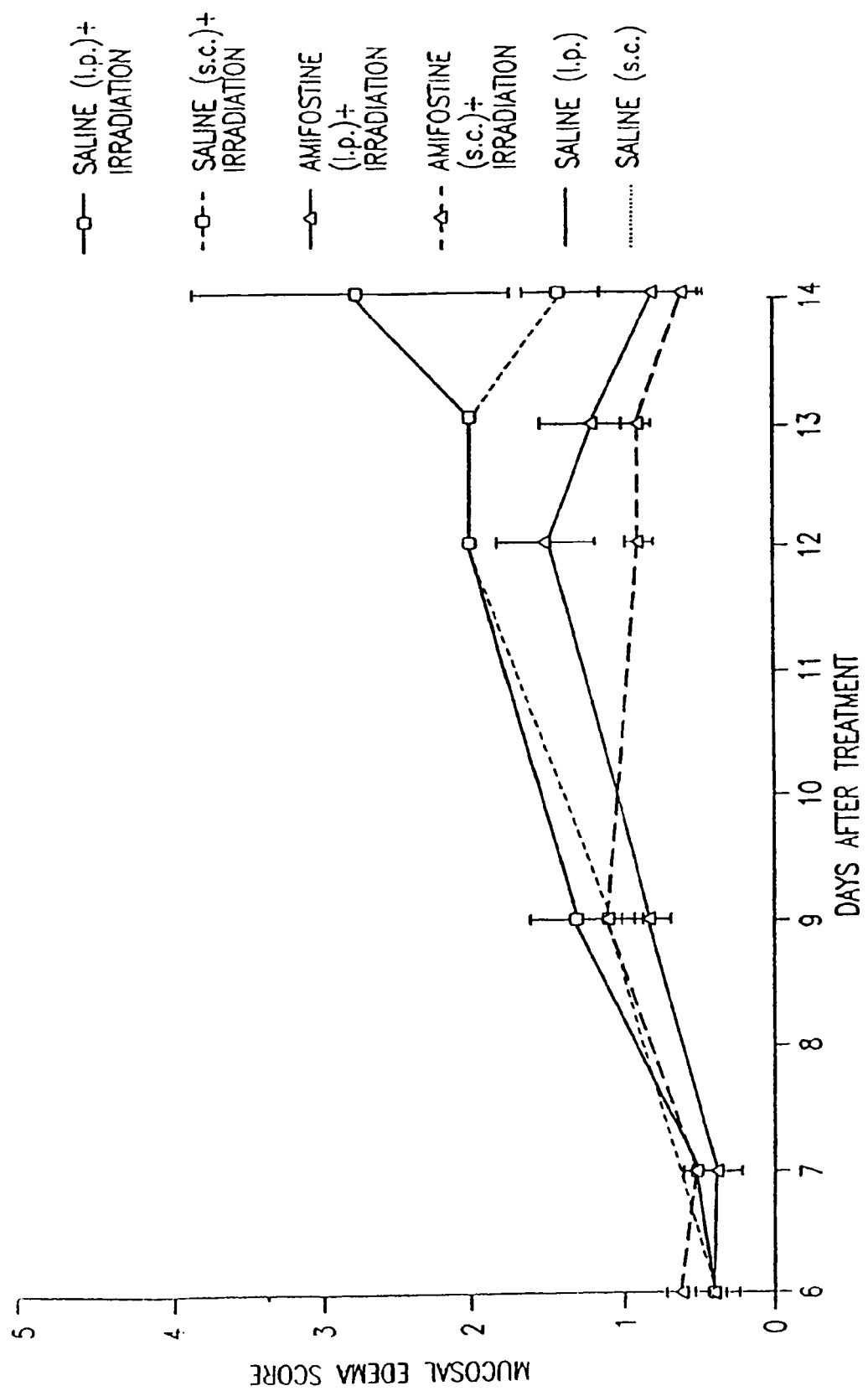

FIGS. 6A and 6B are two graphs of the mucosal edema scores of animals treated with amifostine or saline and a single dose of irradiation at 16.5 Gy. Amifostine and saline were administered by i.p. and s.c. routes. Control animals received saline without irradiation. Amifostine was dissolved at 500 mg in 9.7 ml of 0.9% NaCl to achieve a final concentration of 50 mg/ml. About 0.1-0.2 ml of amifostine was injected in each animal based on the body weight. Amifostine was administered at a dose of 400 mg/kg body weight (FIG. 6A) and at a dose of 200 mg/kg body weight (FIG. 6B).

Figure 7A:
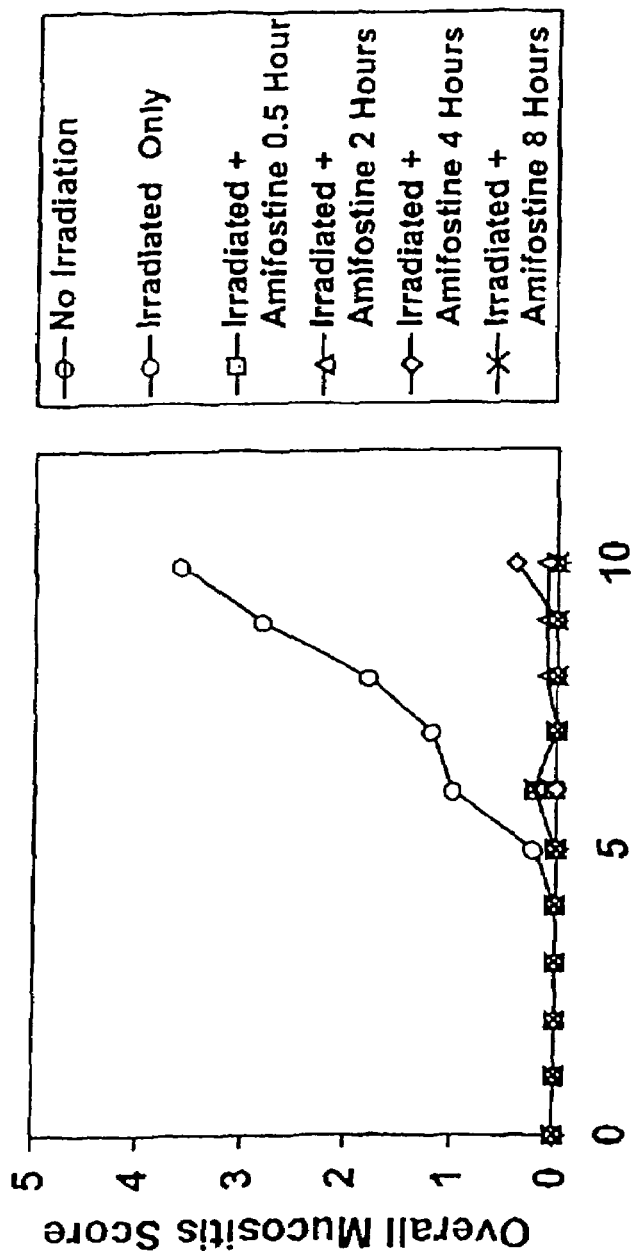

FIG. 7A-7B are two graphs of the overall mucositis scores of animals treated with amifostine prior to a single dose of γ-irradiation at 15.3 Gy. Amifostine and saline were administered by i.v. and s.c. routes. Control animals received saline without irradiation. Amifostine was administered at a dose of 200 mg/kg body weight either intravenously (FIG. 7A) or subcutaneously (FIG. 7B).

5. DETAILED DESCRIPTION OF THE INVENTION

The present invention provides methods of protecting against toxicities associated with anti-cancer therapies in a subject comprising subcutaneously administering to a subject in need thereof an effective amount of amifostine, WR-1065, or a combination thereof at least about 8 hours before the subject is exposed to ionizing radiation. Anti-cancer therapies include, but are not limited to, ionizing radiation therapy or chemotherapy, preferably, ionizing radiation therapy. As used herein, the term "subject" includes mammal, which includes human. The present invention also provides methods of administering amifostine and/or its metabolites to patients in a manner which decreases the undesirable side effects of the compounds as compared to conventional intravenous administration. The invention is based, in part, on the quite unexpected discovery that human patients receiving subcutaneously administered amifostine experienced significantly fewer incidences of nausea, vomiting, headache, hypotension, lightheadedness, somnolence and other undesirable side effects commonly associated with conventional intravenous administration of amifostine than did patients who received amifostine via conventional intravenous infusion. These side effects coincide with the "spike" or "burst" phase of the pharmacokinetic profile of intravenously administered drug.

The invention is further based, in part, on the observation that the pharmacokinetic profiles of amifostine and/or its metabolite WR-1065 for intravenously and subcutaneously administered amifostine are significantly different. Whereas whole blood concentrations of both amifostine and WR-1065 peaked and declined rapidly within the first 10 minutes following intravenous administration of amifostine, whole blood concentrations of both of these compounds increased at a markedly slower rate following subcutaneous amifostine administration, reaching maximum and sustained concentration about 15-45 minutes after administration.

While not intending to be bound by theory, it is believed that the decrease in undesirable side effects observed for subcutaneously administered amifostine as compared to intravenously administered amifostine is in part due to the characteristic pharmacokinetic profile associated with subcutaneous administration. Thus, in the methods of the invention a therapeutically effective amount of amifostine and/or WR-1065 is administered to a patient in a manner such that a characteristic pharmacokinetic profile for either the administered amifostine and/or WR-1065 is obtained, thereby significantly reducing the undesirable side effects suffered by patients receiving such therapy as compared with conventional intravenous administration.

5.1 The Compounds

Compounds that can be advantageously administered according to the methods described herein are amifostine, WR-1065, or combinations thereof, which exhibit selective radioprotection or chemoprotection of normal tissues, and/or bone marrow stimulating or healing activities, and which are suitable for human use with minimal toxicity. Such compounds, as well as pharmaceutically acceptable addition salts and/or hydrates thereof, are either known to those of skill in the art or can be identified without undue experimentation using established tests routinely employed in the art.

The compounds useful in the methods of the invention may be in the form of free acids, free bases, or pharmaceutically acceptable addition salts thereof. Such salts can be readily prepared by treating the compounds with an appropriate acid. Such acids include, by way of example and not limitation, inorganic acids such as hydrohalic acids (hydrochloric, hydrobromic, hydrofluoric, etc.), sulfuric acid, nitric acid, and phosphoric acid, and organic acids such as acetic acid, propanoic acid, 2-hydroxyacetic acid, 2-hydroxypropanoic acid, 2-oxopropanoic acid, propandioic acid, and butandioic acid. Conversely, the salt can be converted into the free base form by treatment with alkali.

The compounds useful in the methods of the invention, as well as the pharmaceutically acceptable addition salts thereof, may be in a hydrated or unhydrated form. Methods of preparing such forms will be apparent to those of skill in the art of organic chemistry.

5.2 Pharmacokinetic Profile

Figure 1:
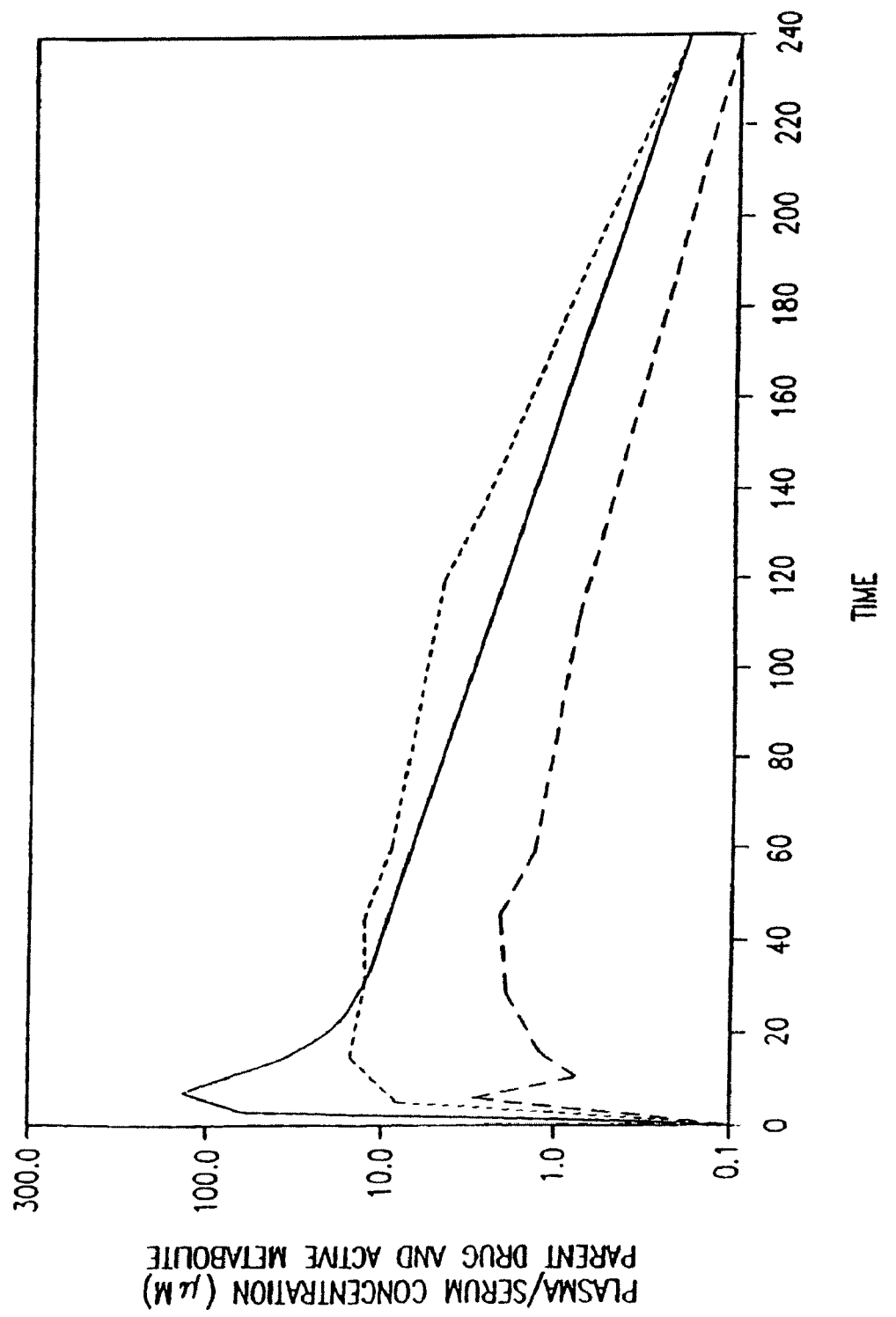
FIG. 1 is a graph of the average whole blood concentration-time curves for amifostine (parent drug WR-2721 plus metabolite WR-1065) following a 500 mg subcutaneous injection, a 500 mg oral solution and a 200 mg/m$^2$ intravenous infusion (over 7.5 minutes) to 12 subjects, 0 to 240 minutes after drug administration (————iv; ---sc; — — —oral).
Figure 2:
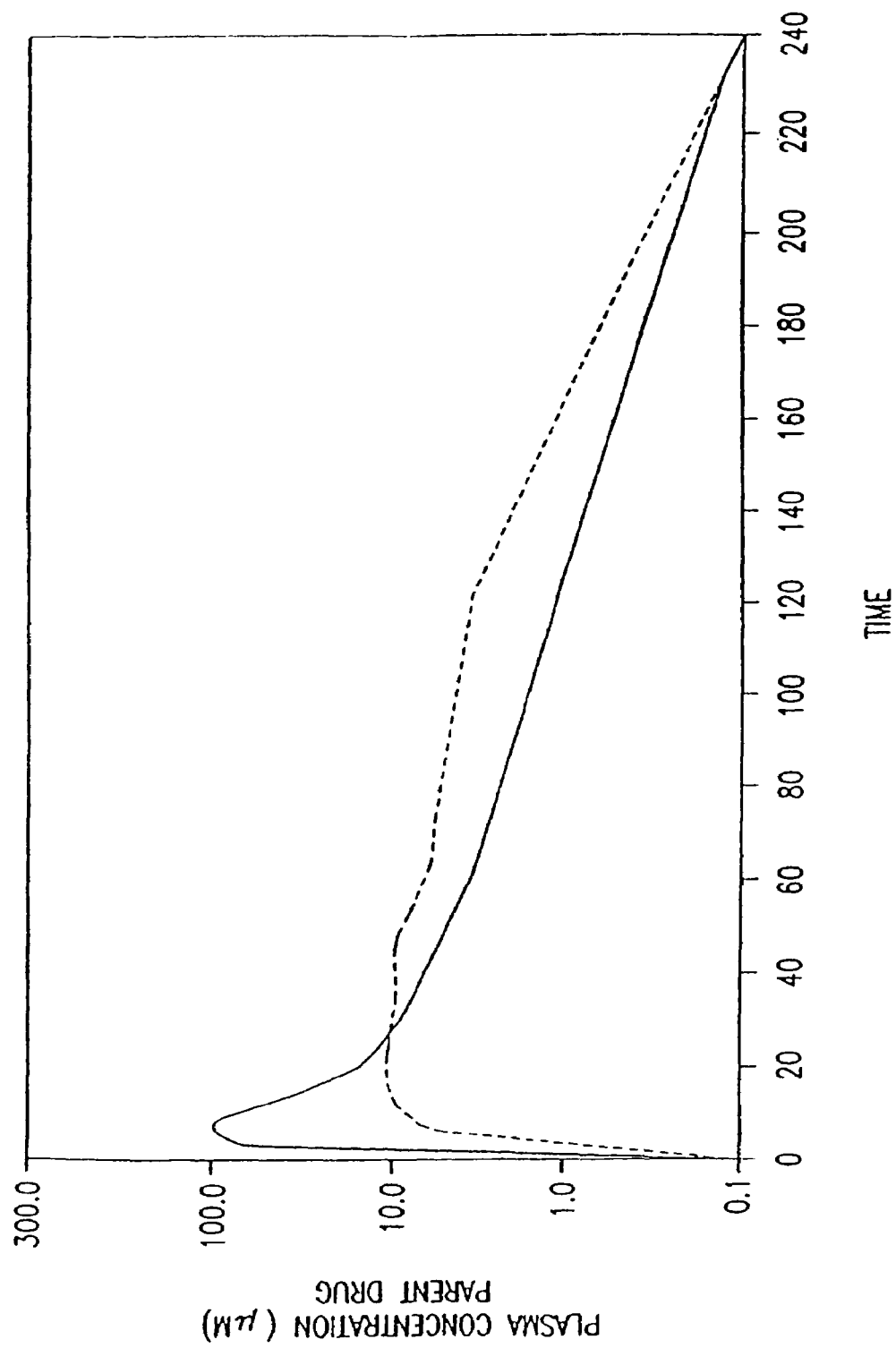
FIG. 2 is a graph of the average plasma concentration-time curves for amifostine (parent drug WR-2721) following a 500 mg subcutaneous injection, and a 200 mg/m$^2$ intravenous infusion (over 7.5 minutes) to 12 subjects, 0 to 240 minutes after drug administration (————iv; ---sc).
Figure 3:
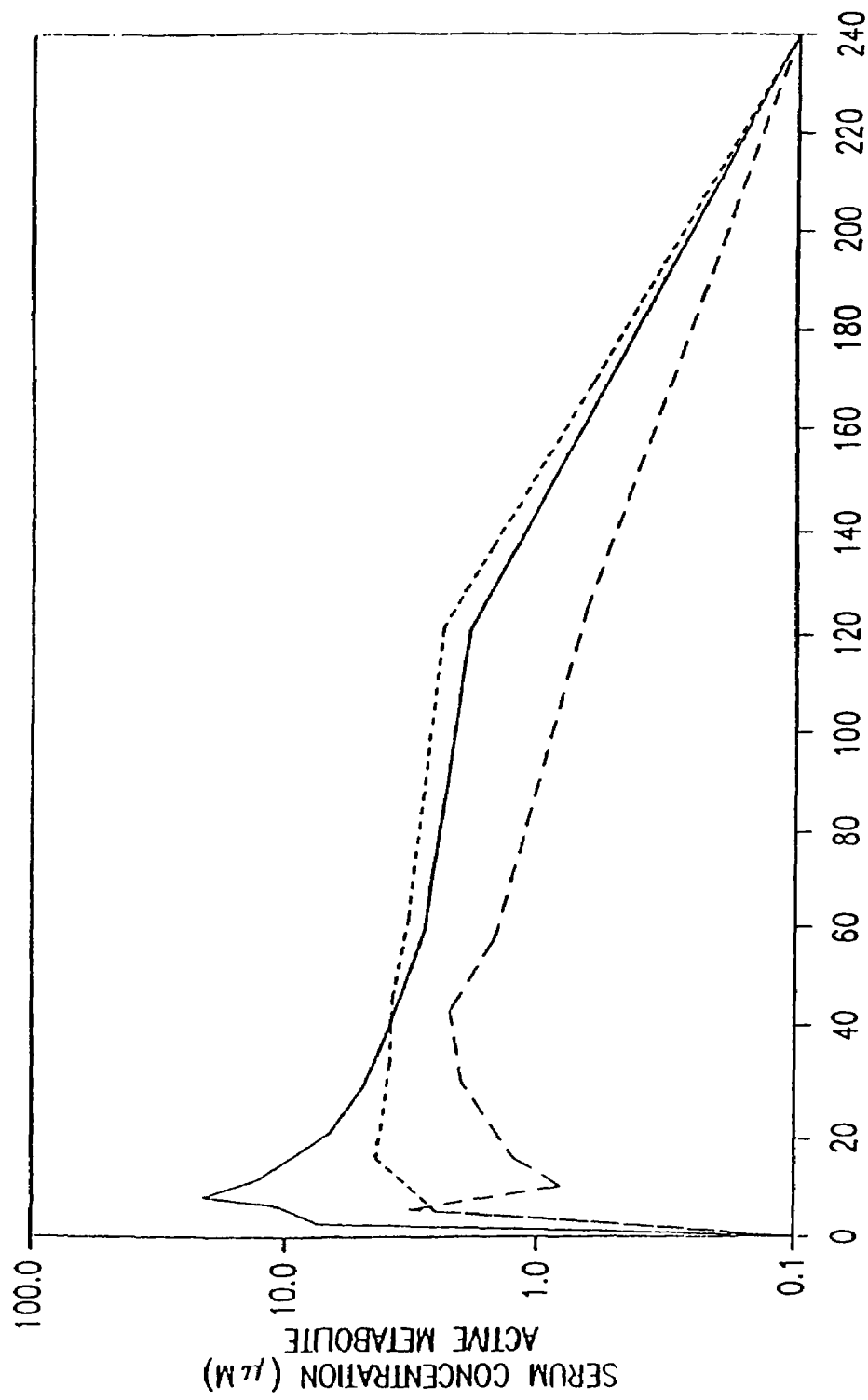
FIG. 3 is a graph of the average serum concentration-time curves for metabolite (WR-1065) following a 500 mg subcutaneous injection, a 500 mg oral solution and a 200 mg/m$^2$ intravenous infusion (over 7.5 minutes) to 12 subjects, 0 to 240 minutes after drug administration (————iv; ---sc; — —oral).

Analysis of the pharmacokinetic profiles of amifostine and WR-1065 following intravenous and subcutaneous administration of amifostine reveals several striking differences. Referring now to FIGS. 1-3, the pharmacokinetic profiles of amifostine (FIG. 2), an metabolite of amifostine (WR-1065) (FIG. 3) and amifostine and WR-1065 combined (FIG. 1) obtained after intravenous administration of amifostine (200 mg/m$^2$ drug infused over 7.5 min.) are characterized by an initial plasma concentration "spike" or "burst" within the first 20 minutes following administration, a time-frame that coincides with the side effect observed clinically: infused drug and/or its metabolite is rapidly taken up within the first minute of administration, reaching a maximum whole blood concentration approximately 8-10 minutes after administration, followed by a rapid (approx. 5-10 fold) decrease in concentration about 10-20 minutes after administration. Following this initial concentration "spike" or "burst," blood levels gradually decrease to zero.

Similar pharmacokinetic profiles were observed with amifostine in cancer patients following a single intravenous bolus dose (150 mg/m$^2$) (Shaw et al., 1986, "Human Pharmacokinetics of WR-2721" *Int. J. Radiat. Oncol. Biol. Phys.* 12:1501-4), a single 15-minute intravenous infusion (up to 910 mg/m$^2$) (Shaw et al., 1988, "Pharmacokinetics of WR-2721" *Pharmac. Ther.* 39:195-201; Shaw et al., 1994, "Pharmacokinetics of Amifostine in Cancer Patients Evidence for Saturable Metabolism" *Proc. Amer. Cos. Clin. Oncol.* 13:144; U.S. Bioscience, 1994, "Pharmacokinetics of Single Dose Amifostine (WR-2721; ETHYOL®)" ETH PK 3) and repeated infusions (up to 910 mg/m$^2$ per dose) (U.S. Bioscience, 1994, "Pharmacokinetics of Double Dose Amifostine (WR-2721; ETHYOL®) with Corresponding Measurements of WR-1065 in Plasma and Bone Marrow Cells" ETH PK 4). In these studies, amifostine was rapidly cleared from the blood, exhibiting a distribution half-life of less than 1 minute and an elimination half-life of approximately 9 minutes.

The pharmacokinetic profiles of amifostine, metabolite WR-1065, and amifostine and WR-1065 combined following subcutaneous administration of amifostine (500 mg dose) differ significantly from those obtained with intravenous administration. First, referring now to FIGS. 1 and 3, maximum whole blood concentrations are not reached by way of an initial concentration spike or burst. Rather, blood concentrations rise at a significantly slower rate, reaching a maximum approximately in 5-60 minutes, preferably 10-40 minutes, after administration. Maximum levels plateau, being maintained for about 10 to 130 minutes, preferably about 15 to 120 minutes, before gradually decreasing to baseline levels.

Additionally, the maximum whole blood concentrations of both amifostine and WR-1065 were significantly lower following subcutaneous administration than intravenous administration. For example, for intravenous administration, peak levels for amifostine and WR-1065 were about 100 μM and about 23 μM, respectively. For subcutaneous administration, maximum blood levels for amifostine and WR-1065 were about 12 μM and 4 μM, respectively. These concentrations are biologically effective, both as a cytoprotective agent and in MDS (Dorr et al., 1995, Eur. J. Cancer 31a (supp. 5):579, List et al., 1995, Blood 86(10) Supp. 1:1327 (Abstract)).

Thus, the advantageous pharmacokinetic profiles of the invention are generally characterized by three main features: (i) a first region wherein the plasma and/or whole blood concentration of administered amifostine and/or its metabolite WR-1065 slowly rises to a maximum level; (ii) a second region wherein the maximum plasma and/or whole blood concentration of administered amifostine and/or its metabolite WR-1065 plateaus; and (iii) a third region wherein the maximum plasma and/or whole blood concentration of administered amifostine and/or its metabolite WR-1065 slowly decreases to baseline levels.

In the first region of the pharmacokinetic profile, the plasma and/or blood concentration usually increases at a rate of about 0.1 μM/min. to 40 μM/min., preferably about 0.3 μM/min. to 20 μM/min., and most preferably about 0.5 μM/min. to 10 μM/min. This increase toward the maximum concentration usually occurs over a period of about 1 min. to 60 min., commonly over a period of about 5 min. to 25 min., typically over a period of about 10 min. to 20 min., and preferably over a period of about 15 min. The maximum plasma and/or blood concentration is usually reached in about 5 to 60 min. following administration, and is preferably reached about 12 min. to 18 min. following administration. The increase in plasma and/or blood concentrations in this first region is usually zero-order, i.e., the rate of increase is substantially constant during the period of rise.

The maximum plasma and/or blood concentration of administered amifostine and/or WR-1065 reached at the end of the first region remains relatively constant, i.e. plateaus, in the second region of the pharmacokinetic profile. Preferably, the plasma and/or blood concentration does not fluctuate by more than about ±75%. More preferably, the plasma and/or blood concentration does not fluctuate by more than ±35%. The plateau is usually maintained for about 10 min. to 130 min., preferably about 15 min. to 120 min., and occurs about 15 min. to 80 min. after administration.

In the third region, the plasma and/or blood concentration of administered amifostine and/or WR-1065 slowly decreases towards baseline levels. The rate of decrease in plasma and/or blood concentration is typically governed by the subject's metabolism, and is not believed to be a critical feature towards effecting a reduction or decrease in undesirable side-effects following administration. While the actual rate of decrease in the plasma and/or blood concentration of administered compound (or metabolites thereof) will vary from subject to subject, the concentration usually decreases at a rate of about 0.001 NM/min. to 0.2 μM/min., over a period of about 30 min. to 220 min. The third region usually occurs about 60 min. to 180 min. following administration.

While not intending to be bound by any particular theory, it is believed that the reduction or decrease in adverse side-effects following administration is due to the characteristics of the above-described pharmacokinetic profile. The slow rate at which the plasma and/or blood concentration of administered amifostine and/or WR-1065 increases to maximum, as well as maintenance of the maximum level for a period of time, are thought to be of particular importance. Thus, it is believed that the pharmacokinetic profiles of the invention decrease or reduce adverse side effects of amifostine and/or WR-1065 by eliminating the initial "spike" or "burst" in amifostine and/or WR-1065 and/or blood concentrations that are associated with conventional intravenous administration, and that are likely unnecessary for efficacy.

The actual maximum plasma and/or blood concentration of administered amifostine and/or WR-1065 is not believed to be of critical importance in reducing or decreasing adverse side-effects. As long as the compounds are administered according to the pharmacokinetic profiles described herein, a reduction or decrease in undesirable side-effects should be observed regardless of the actual maximum plasma and/or blood concentration reached. Thus, as will be discussed in more detail in a later section, virtually any amount of amifostine and/or WR-1065 that yields a plasma and/or whole/blood concentration of the administered amifostine and/or its metabolite WR-1065, that is therapeutically effective can be advantageously administered according to the pharmacokinetic profiles described herein. The maximum plasma and/or blood concentration will usually range from about 1 μM to 40 μM.

5.3 Uses of the Methods

The methods of the invention can be used to efficaciously administer amifostine and/or WR-1065 to patients to treat virtually any disorder that is now known or that is later discovered to be treatable with such compounds.

For example, as the compounds described herein are able to selectively protect normal tissues against the toxicities associated with ionizing radiation without adversely affecting the tumor response (Constine et al., 1986, "Protection by WR-2721 of Human Bone Marrow Function Following Irradiation" Int. J. Radia. Oncol. Biol. Phys. 12:1505-8; Liu et al., 1992, "Use of Radiation with or Without WR-2721 in Advanced Rectal Cancer" Cancer 69(11):2820-5; Wadler et al., 1993, "Pilot Trial of Cisplatin, Radiation and WR-2721 in Carcinoma of the Uterine Cervix: A New York Gynecologic Oncology Group Study" J. Clin. Oncol. 11(8):1511-6; Büntzel et al., 1996, "ETHYOL® (Amifostine) Provides Multilineage heatoprotection and Protection Against Nonhematologic Toxicities Reduced by Radiochemotherapy (RCT) of Head and Neck Cancer," Blood 88 (10) Supp. 1:448a [1781] [Abstract]), the methods described herein can be used to administer the compounds to cancer patients receiving radiation therapy or chemotherapy. Administering amifostine and/or WR-1065 to patients receiving radiation therapy or chemotherapy can protect the patients against the toxicities associated with the exposure to the therapy. These toxicities include, but are not limited to, neurotoxicity, nephrotoxicity, ototoxicity, cardiotoxicity, alopecia, mucositis, and include xerostomia, infertility, pulmonary toxicity, and renal failure that can occur in severe cases. Amifostine and/or its metabolite WR-1065 are particularly effective in preventing mucositis and xerostomia. Amifostine and/or its metabolite WR-1065 are also effective at treating acute xerostomia and late xerostomia and acute mucositis and late mucositis. In particular the methods described herein can be used to administer amifostine and/or its metabolite WR-1065 to patients receiving radiation therapy for head and neck cancer.

The term "xerostomia," as used herein means dryness of mouth due to salivary gland dysfunction induced by radiation. The term "acute xerostomia," as used herein means xerostomia occurring within 90 days of treatment initiation, characterized by dryness of mouth with thick, sticky saliva, altered taste, or acute salivary gland necrosis. The term "late xerostomia," as used herein means xerostomia occurring 90 days to 2 years after treatment initiation, characterized by dryness, poor saliva production, or fibrosis of salivary glands.

The term "mucositis," as used herein means inflammation of mucosal membranes induced by radiation or chemotherapy. The term "acute mucositis," as used herein means mucositis occurring within 90 days of treatment initiation, characterized by parchy or confluent pseudomembranes, ulceration, or necrosis. The term "late mucositis," as used herein means mucositis: occurring 90 days to 2 years after treatment initiation, characterized by mucosal atrophy, dryness, telangiectasia or ulceration.

Amifostine and/or its metabolite WR-1065 are also capable of selectively protecting normal tissues from the toxicities associated with cancer chemotherapeutic agents, including but not limited to, alkylating agents, platinum agents, anthracyclines and taxanes (Kemp et al., 1996, "Amifostine Pretreatment for Protection Against Cyclophosphamide-and Cisplatin-Induced Toxicities Results of A Randomized Control Trial in Patients with Advanced Ovarian Cancer" *J. Clin. Oncol.* 14:2101-12; Wasserman et al., 1981 "Differential Protection Against Cytotoxic Chemotherapeutic Effects on Bone Marrow CFUs by WR-2721" *Cancer Clin. Trials* 4:3-6; Glover et al., 1986, "WR-2721 Protects Against the Hematologic Toxicity of Cyclophosphamide: A Controlled Phase II Trial" *J. Clin. Oncol.* 4:584-8; Schiller et al., 1996, "Amifostine, Cisplatin and Vinblastine in Metastic Nonsmall Cell Lung Cancer: A Report of High Response Rates and Prolonged Survival" *J. Clin. Oncol.* 14:1913-21; Dorr et al., 1995, "Selective Cardioprotection of Rat Heart Myocytes Exposed to DNA Zutercalating Agents Using Amifostine (AMI) and It's Dephospharylated Metabolite, WR-1065," *Eur. J. Cancer* 31a(Supp. 5):579; Betticher et al., 1995, "Carboplatin Combined with Amifostine, a Bone Marrow Protectant, in the Treatment of Non-Small Cell Lung Cancer: A Radomised Phase II Study" *Br. J. Cancer* 5:1551-5; DiPaola et al., 1996, "A Phase I Study of Amifostine and Paclitaxel in Patients with Advanced Malignancies" *Proc. Amer. Soc. Clin. Oncol.* 15:488 (1556) Abstract). Thus, the methods of the invention can also be used to advantageously administer amifostine and/or its metabolite WR-1065 to cancer patients receiving chemotherapy.

Amifostine and/or WR-1065 are also capable of stimulating bone marrow growth (WO 96/25045) and causing the bone marrow function to more rapidly recover following chemotherapy (List et al., "Amifostine Stimulated Formation of Multipotent Progenitor and Generated Macroscopic Colonies in Normal and Myelodysplastic Bone Marrow," *Proc. Am. Soc. Clin. Oncol.* 15:449 [1403] [Abstract]; List et al., 1996, "Amifostine Protects Primitive Hematopoietic Progenitors Against Chemotherapy Cytotoxicity," *Semin. Oncol.* 23 (4) Supp. 8:58-63). Thus, the methods of the invention further provide a useful means for administering amifostine and/or WR-1065 to patients suffering from diseases requiring bone marrow growth, such as myelodysplastic syndrome (MDS), and to patients whose bone marrow has been exposed to chemotherapy. In addition, the methods of the invention also provide a useful means for administering amifostine and/or WR-1065 to patients suffering from cancer and human immunodeficiency virus infection.

Administering amifostine and/or WR-1065 to patients according to the methods of the invention provides myriad advantages over currently available intravenous modes of administration. A significant advantage is the reduction or decrease in undesirable side-effects suffered by patients receiving the therapy. Additionally, since the methods do not require i.v. injection, which is the mode of administration most disliked by patients, the methods described herein will generally provide better patient compliance. Further, the methods of the invention do not necessarily require administration by skilled practitioners, making the therapy more convenient for patients.

5.4 Formulation and Routes of Administration

Amifostine and/or WR-1065, or pharmaceutically acceptable addition salts or hydrates thereof, can be delivered to a patient so as to avoid or reduce undesirable side effects according to the invention using a wide variety of routes or modes of administration. The only requirement is that amifostine and/or WR-1065, be delivered according to the pharmacokinetic profiles described herein. Suitable routes of administration include, but are not limited to, inhalation, transdermal, oral, rectal, transmucosal, intestinal and parenteral administration, including intramuscular, subcutaneous and intravenous injections.

For any mode of administration, the actual amount of amifostine and/or WR-1065 delivered, as well as the dosing schedule necessary to achieve the advantageous pharmacokinetic profiles described herein, will be depend, in part, on such factors as the bioavailability of amifostine and/or WR-1065, the disorder being treated, the desired therapeutic dose, and other factors that will be apparent to those of skill in the art. The actual amount delivered and dosing schedule can be readily determined by those of skill without undue experimentation by monitoring the blood plasma levels of administered amifostine and/or WR-1065, and adjusting the dosage or dosing schedule as necessary to achieve the desired pharmacokinetic profile.

For example, for intravenous administration the advantageous profiles of the invention can be obtained by utilizing a significantly slower rate of infusion than is conventionally used, or by using an ambulatory pump. Methods of obtaining the desired pharmacokinetic profiles via other modes of administration will be apparent to those of skill in the art, especially in light of the detailed disclosure provided herein.

Amifostine and/or WR-1065, or pharmaceutically acceptable salts and/or hydrates thereof, may be administered singly, in combination with other compounds, and/or in combination with other therapeutic agents, including cancer chemotherapeutic agents. Amifostine and/or WR-1065 may be administered alone or in the form of a pharmaceutical composition, wherein amifostine and/or WR-1065 is in admixture with one or more pharmaceutically acceptable carriers, excipients or diluents. Pharmaceutical compositions for use in accordance with the present invention may be formulated in conventional manner using one or more physiologically acceptable carriers comprising excipients and auxiliaries which facilitate processing of amifostine and/or WR-1065 into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, amifostine and/or WR-1065 can be formulated readily by combining amifostine and/or WR-1065 with pharmaceutically acceptable carriers well known in the art. Such carriers enable amifostine and/or WR-1065 to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of amifostine and/or WR-1065 doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, amifostine and/or WR-1065 for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Amifostine and/or WR-1065 may be formulated for parenteral administration by injection, e.g., by bolus injection or continuous infusion. It is preferred that amifostine and/or WR-1065 be administered by continuous infusion subcutaneously over a period of 15 minutes to 24 hours. Formulations for injection may be presented in unit dosage form, e.g., in ampoules or in multi-dose containers, with an added preservative. Amifostine and/or WR-1065 may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of amifostine and/or WR-1065 in water-soluble form. Additionally, suspensions of amifostine and/or WR-1065 may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

Amifostine and/or WR-1065 may also be formulated in rectal compositions such as suppositories or retention enemas, e.g., containing conventional suppository bases such as cocoa butter or other glycerides.

In addition to the formulations described previously, amifostine and/or WR-1065 may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

5.5 Effective Dosages

Pharmaceutical compositions suitable for use with the present invention include compositions wherein the active ingredient is contained in a therapeutically effective amount, i.e., an amount effective to achieve its intended purpose. Of course, the actual amount of active ingredient will depend on, among other things, its intended purpose. For example, when administered to cancer patients as a cytoprotectant in conjunction with radiation or chemotherapy, such compositions will contain an amount of active ingredient effective to, inter alia, ameliorate the harmful effects of ionizing radiation or chemotherapeutic agents to normal tissues. When administered to patients suffering from diseases requiring bone marrow growth, such as MDS, or more rapid recovery of bone marrow function following chemotherapy, such compositions will contain an amount of active ingredient effective to stimulate bone marrow production or function, prevent the development of or alleviate the existing symptoms of, or prolong the survival of, the patient being treated. Determination of an effective amount is well within the capabilities of those skilled in the art, especially in light of the detailed disclosure herein.

For any compound described herein the therapeutically effective amount can be initially estimated from cell culture assays. For example, a dose can be formulated in animal models to achieve a circulating concentration range of compound, and/or an metabolite thereof, that includes an effective concentration as determined in cell culture. Such information can be used to more accurately determine useful doses in humans. See, e.g., Washburn et al., 1976, "Prediction of the Effective Radioprotective Dose of WR-2721 in Humans Through an Interspecies Tissue Distribution Study" *Radiat. Res.* 66:100-5.

Therapeutically effective amounts for use in humans can also be estimated from animal models. For example, a dose for humans can be formulated to achieve a circulating concentration found to be effective in animals.

A therapeutically effective dose can also be estimated from human pharmacokinetic data. While not intending to be bound by any particular theory, it is believed that efficacy is related to a subject's total exposure to an applied dose of administered drug, and/or an metabolite thereof, as determined by measuring the area under the blood concentration-time curve (AUC). Thus, a dose administered according to the methods of the invention that has an AUC of administered compound (and/or an metabolite thereof) within about 50% of the AUC of a dose known to be effective for the indication being treated is expected to be effective. A dose that has an AUC of administered compound (and/or an metabolite thereof) within about 70%, 80% or even 90% or more of the AUC of a known effective dose is preferred. Adjusting the dose to achieve maximal efficacy in humans based on the methods described above, particularly on the blood concentration and duration of administered compound and/or its metabolites is well within the capabilities of the ordinarily skilled artisan.

For use as a cytoprotectant to selectively protect against the toxicities of ionizing radiation or chemotherapeutic agents, a circulating concentration of administered compound (and/or and metabolite thereof) of about 2 µM to 100 µM is expected to be effective, with about 5 µM to 50 µM being preferred. Alternatively, or in addition, a tissue concentration of administered compound (and/or an metabolite thereof) of about 4 µM to 700 µM is expected to be effective, with about 20 µM to 350 µM being preferred.

Usual patient doses for administration of amifostine and/or WR-1065 usually range from about 50 mg/day to 6000 mg/day, commonly from about 100 mg/day to 4000 mg/day, and typically from about 200 mg/day to 3500 mg/day. Stated in terms of patient body weight, usual dosages range from about 0.6 to 100 mg/kg/day, commonly from about 1.1 to 66 mg/kg/day, and typically from about 2.2 to 58 mg/kg/day. Stated in terms of patient body surface areas, usual dosages range from about 23 to 4000 mg/m$^2$/day, commonly from about 45 to 2666 mg/m$^2$/day, and typically from about 90 to 2333 mg/m$^2$/day.

For subcutaneous administration of amifostine and/or WR-1065 patient dosages usually range from about 50 mg/day to 1500 mg/day, commonly from about 100 mg/day to 1000 mg/day and typically from about 200 mg/day to 750 mg/day. Stated in terms of body weight, usual dosages range from 0.5 mg/kg/day to 25 mg/kg/day, commonly from about 1 mg/kg/day to 16 mg/kg/day and typically from about 3.3 mg/kg/day to 12.5 mg/kg/day. Stated in terms of patient body surface areas, usual doses range from about 22 mg/m$^2$/day to 1000 mg/m$^2$/day, commonly from about 45 mg/m$^2$/day to 666 mg/m$^2$/day and typically from about 133 mg/m$^2$/day to 500 mg/m$^2$/day.

For use as a radioprotectant against the toxicities of ionizing radiation, including, but not limited to, xerostomia or mucositis, or as a chemoprotectant against the toxicities of cancer therapy, such as head and neck cancer, the dose should be administered enough in advance of exposure to radiation or chemotherapy to provide effect. For subcutaneous administration, the dose is preferably administered within at least about 3 hours prior to the administration of radiation therapy. Preferably the dose is subcutaneously administered at least about 6 hours prior to the administration of radiation therapy, more preferably at least about 8 hours, and most preferably about 8 to about 12 hours prior to the administration of radiation therapy.

Administering the amifostine and/or WR-1065 are particularly useful in treating the toxicities associated ionizing radiation, especially in patients with head and neck cancer. In these cases subcutaneous administration is preferable and is most effective at reducing side effects.

For use in treating diseases requiring bone marrow growth, such as MDS, or recovery of bone marrow function, a circulating concentration of administered compound (and/or an metabolite thereof) of about 2 µM to 100 µM is expected to be effective. Alternatively, or in addition, a tissue concentration of administered compound (and/or an metabolite thereof) of about 0.1 µM to 1000 µM is expected to be effective, with about 10 µM to 500 µM being preferred.

Usual patient doses for administration of amifostine and/or WR-1065 usually range from about 50 mg/day to 1000 mg/day, commonly from about 100 mg/day to 900 mg/day, and typically from about 200 mg/day to 800 mg/day. Stated in terms of patient body weight, usual dosages range from about 0.5 to 16 mg/kg/day, commonly from about 1.1 to 15 mg/kg/day, and typically from about 2.2 to 13.5 mg/kg/day. Stated in terms of patient body surface areas, usual dosages range from about 22 to 666 mg/m$^2$/day, commonly from about 45 to 600 mg/m$^2$/day, and typically from about 90 to 540 mg/m$^2$/day.

For subcutaneous administration of amifostine and/or WR-1065 patient dosages usually range from about 50 mg/day to 1200 mg/day, commonly from about 100 mg/day to 1100 mg/day and typically from about 200 mg/day to 1000 mg/day. Stated in terms of body weight, usual dosages range from 0.5 mg/kg/day to 20 mg/kg/day, commonly from about 1.1 mg/kg/day to 18 mg/kg/day and typically from about 2.2 mg/kg/day to 16.2 mg/kg/day. Stated in terms of patient body surface areas, usual doses range from about 22 mg/m$^2$/day to 800 mg/m$^2$/day, commonly from about 45 mg/m$^2$/day to 720 mg/m$^2$/day and typically from about 90 mg/m$^2$/day to 650 mg/m$^2$/day.

For use as a radioprotectant against the toxicities of ionizing radiation, the dose is preferably at least about 500 mg, preferably about 500 mg to 1500 mg administered subcutaneously. Preferably, the dose is administered as two subcutaneous injections.

For other modes of administration, dosage amount and interval can be adjusted individually to provide effective plasma and/or tissue levels of the administered compound, and/or an metabolite thereof, according to the pharmacokinetic profiles described herein, as previously described.

The actual amount of composition administered will, of course, be dependent on the subject being treated, the subject's weight, the severity of the affliction, the mode of administration and the judgement of the prescribing physician.

6. EXAMPLE

Subcutaneous Administration of Amifostine

Reduces In Vivo Toxicities

The advantageous effects of subcutaneously administering amifostine to patients was demonstrated in a Phase I, randomized three-way crossover study. The study was conducted at one site in the United States.

Normal subjects were randomized to receive amifostine for three successive days as an intravenous infusion (200 mg/m$^2$), an oral formulation (500 mg) and a subcutaneous injection (500 mg) as described in TABLE 1. A total of 12 subjects were treated in the study.

TABLE 1

Treatment Scheme
(Three-Way Crossover Design)

|  | Day 1 | Day 2 | Day 3 |
|---|---|---|---|
| Sequence 1 | A | B | C |
| Sequence 2 | B | C | A |
| Sequence 3 | C | A | B |

Treatment A: Amifostine (200 mg/m$^2$) as a continuous intravenous infusion over 7.5 minutes.
Treatment B: Amifostine (500 mg) in liquid formulation as a single oral dose.
Treatment C: Amifostine (500 mg) as two simultaneous subcutaneous injections.

All subjects were sequestered at the study site from the evening before the administration of the first dose of study drug until the final whole blood sample was obtained. Whole blood samples were collected up to 4 hours after each dose of amifostine.

Eligible subjects included healthy, normal male volunteers between the ages of 18 and 35 years (inclusive). All subjects who entered the study had pretreatment values for complete blood counts (CBC), serum chemistries and urinalysis within ±10% of the normal range for the referring laboratory which were considered clinically insignificant by the inventors. Additionally, all subjects had a normal pretreatment electrocardiogram (EKG).

Subjects who were known to be human immunodeficiency virus (HIV) positive, active substance abusers or smokers (at least within the past 6 months) were excluded. Also excluded were subjects with pretreatment hypertension (systolic blood pressure >140 mm Hg), subjects with known cardiovascular disease, subjects with general or psychological conditions which would preclude them from completing the study or signing the informed consent, and subjects who were unwilling or unable to abstain from alcoholic beverages and all medications, including prescription and over-the-counter drugs and vitamins, for 7 days prior to study entry and for 3 days while participating in the study.

6.1 Preparation of Intravenous Amifostine

For intravenous infusion, each vial of amifostine (500 mg per vial, U.S. Bioscience, lot. no. C3017C) was reconstituted with 9.7 mL of 0.9% Sodium Chloride Injection, USP. The appropriate dose of amifostine (200 mg/m$^2$) was further diluted with 0.9% Sodium Chloride Injection, USP, to produce a volume of 50 mL for administration.

6.2 Preparation of Oral Amifostine

For oral administration, each vial of amifostine (500 mg per vial, U.S. Bioscience, lot. no. C3017C) was reconstituted with 5 mL of normal saline solution. The reconstituted solution was drawn up in a 10 mL syringe for administration.

6.3 Preparation of Subcutaneous Amifostine

For subcutaneous injection, each vial of amifostine (500 mg per vial, U.S. Bioscience, lot. no. C3017C) was reconstituted with 2.5 mL of normal saline solution. This solution was divided into two syringes (1.25 mL per syringe) for administration.

6.4 Administration of Intravenous Amifostine

Subjects received intravenous amifostine at a dose of 200 mg/m$^2$ as a 7.5 minute infusion (via an infusion pump) beginning at 8:00 AM. During the infusion, the subjects were kept in a supine position. Following amifostine administration, all subjects were allowed to have a standard breakfast. Moreover, all subjects were given a standard lunch at noon, a standard dinner at 6:00 PM and a standard snack at 10:00 PM.

Baseline systolic blood pressure and pulse were measured just prior to the amifostine infusion, every 2.5 minutes during the infusion and 5 minutes after the infusion. The amifostine infusion was interrupted if systolic blood pressure decreased as outlined in TABLE 2, or if the subject developed symptoms related to decreased blood pressure (dizziness, diaphoresis or chest pain).

If hypotension occurred, the subject was to receive a rapid infusion of normal saline and was to be kept supine or in the Treudelenburg position until the blood pressure returned to baseline. During this time, blood pressure was monitored every 3 minutes.

If blood pressure returned to the value stipulated in TABLE 2 within 5 minutes of stopping the amifostine infusion, and the subject was otherwise asymptomatic, the amifostine infusion could be restarted with continued frequent monitoring of blood pressure. If any further episode of hypotension occurred, the above guidelines were to be reapplied. If a subject's blood pressure did not return to the threshold value for restarting the amifostine infusion within 5 minutes of stopping the amifostine infusion, the infusion was to be stopped and any unused drug was discarded.

TABLE 2

Blood Pressure Guidelines for Interrupting and Starting Amifostine

|  | Baseline Systolic Blood Pressure (mm Hg) | | | |
|---|---|---|---|---|
|  | ≦110 | 111-130 | 131-150 | >170 |
| Stop infusion if systolic blood pressure decreases to: | ≦80 | ≦100 | ≦105 | ≦130 |
| Re-start infusion when systolic blood pressure returns to: | >80 | >100 | >120 | >130 |

6.5 Administration of Oral Amifostine

Subjects receiving oral amifostine were to fast (except for water) beginning at midnight the night before receiving the oral dose until noon of the following day when they received a standard lunch. On the day subjects received oral amifostine, ranitidine (50 mg) was administered by intravenous injection 1 hour prior to the start of amifostine administration.

Subjects received oral amifostine at a dose of 500 mg in a liquid formulation. This formulation was administered by gently squirting the solution in the back of the subject's throat. Subjects were kept in a supine position for 1 hour following administration of the oral solution of amifostine. Following administration of amifostine, all subjects were allowed to drink 4 oz. of water and to eat hard candy to ameliorate any unpleasant taste from oral amifostine. All subjects were given a standard lunch at noon, a standard dinner at 6:00 PM and a standard snack at 10:00 PM.

Vital signs (blood pressure and pulse) were measured just prior to oral administration of amifostine and repeated every 5 minutes for 1 hour. If hypotension occurred, the subject was to receive a rapid infusion of 500 mL normal saline and was to be kept supine or in the Trendelenburg position until blood pressure returned to baseline. During this time, blood pressure was monitored every 3 minutes.

6.6 Administration of Subcutaneous Amifostine

Subcutaneous amifostine was administered at a dose of 500 mg (as a liquid formulation). The dose of amifostine was divided equally into two syringes and administered into two locations on the abdominal wall. Subjects were kept supine for 30 minutes following the two injections of amifostine.

Following amifostine administration, all subjects were allowed to have a standard breakfast. All subjects were given a standard lunch at noon, a standard dinner at 6:00 PM and a standard snack at 10:00 PM.

Vital signs (blood pressure and pulse) were measured just prior to subcutaneous administration of amifostine and repeated every 5 minutes for 30 minutes. If hypotension occurred, the subject was to receive a rapid infusion of 500 mL normal saline and was to be kept supine or in the Trendelenburg position until blood pressure returned to baseline. During this time, blood pressure was monitored every 3 minutes.

6.7 Prior and Concomitant Medications

Ranitidine was administered to all subjects on the day amifostine was administered orally. Any subject who experienced Grade 2 or higher nausea and/or vomiting was allowed to receive prochlorperzaine (10 mg orally or by suppository) every 4 hours as needed.

6.8 Pretreatment Assessments

Pretreatment evaluations were performed within 7 days of initiating treatment and included the following:
 history and physical exam including height, weight and vital signs (blood pressure, pulse and temperature);
 CBC with differential and platelets;
 blood chemistries including blood urea nitrogen (BUN), serum creatinine, calcium, total bilirubin, albumin, SGOT, SGPT, alkaline phosphate, glucose and total protein;
 urinalysis; and
 EKG.

If any subject's laboratory parameters were abnormal, the laboratory tests were repeated. If upon retest the parameters were normal, the subject was included in the study. If the abnormal parameters persisted, the subject was excluded from the study.

6.9 Efficacy Assessments

The primary endpoint of this study was the relative bioavailability of 500 mg of amifostine administered subcutaneous or orally compared to 200 mg/m² of amifostine administered intravenously. As this was a crossover study in which each subject received amifostine by all three routes of administration, the bioavailabilities of subcutaneous and oral amifostine relative to intravenous amifostine were assessed within each subject.

6.9.1 Collection of Blood Samples

Blood samples (5 to 7 mL each) were collected either by venipuncture or indwelling venous catheter (IVC) heparin lock. If IVC was used, it was inserted in the arm opposite the infusion site. If central line was used, intravenous amifostine was administered by a distal intravenous site. For either line, the first 3 to 5 cc of blood were discarded (void volume) prior to blood collection.

For subjects receiving intravenous amifostine, blood samples were collected 5 minutes prior to amifostine administration (baseline) and 2.5, 5, 7.5, 10, 15, 20, 30 and 60 minutes, and 2 and 4 hours after amifostine administration.

For subjects receiving oral amifostine as a liquid formulation, blood samples were collected immediately prior to amifostine administration (baseline) and 5, 10, 15, 30, 45 and 60 minutes, and 2 and 4 hours after amifostine administration.

For subjects receiving subcutaneous amifostine, blood samples were collected immediately prior to amifostine administration (baseline) and 5, 10, 15, 30, 45 and 60 minutes, and 2 and 4 hours after amifostine administration.

6.9.2 Blood Sample Preparation

Blood samples were collected at specified times during a 4-hour period after each dose of amifostine. Each blood sample was prepared as described in TABLE 3. Blood samples were divided for purposes of analysis: one sample was used to determine the presence of amifostine, and the other sample was used to determine the presence of WR-1065 (metabolite).

TABLE 3

Preparation of Plasma Samples for Determination of Concentrations of Amifostine and WR-1065

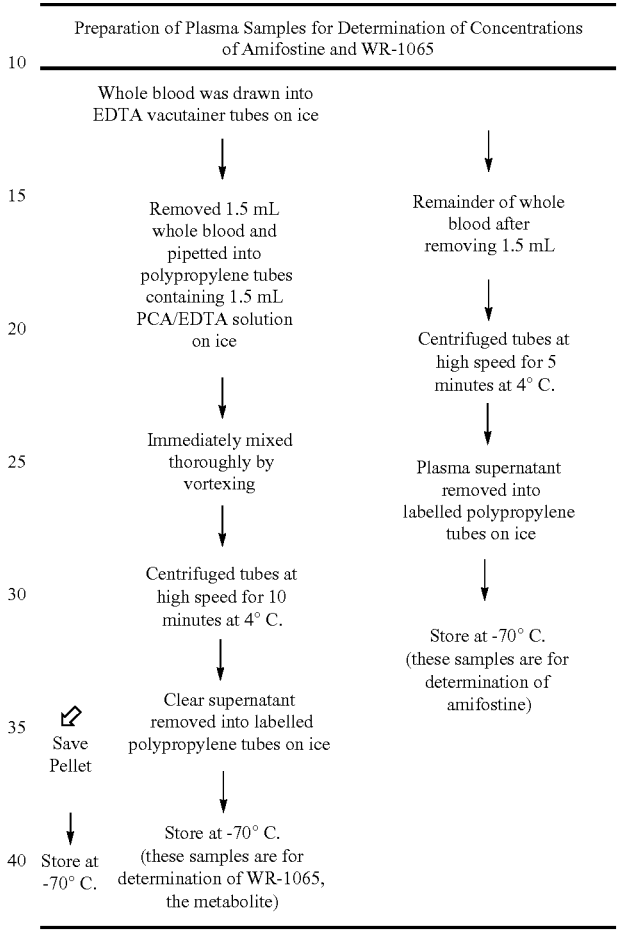

EDTA is ethylenediaminetetraacetic acid
PCA is perchloric acid

As shown in TABLE 3, the preparation of amifostine (parent drug) and WR-1065 (metabolite) for pharmacokinetic analysis differed from one another. This difference was based on the metabolic pathway of amifostine. Amifostine is a prodrug that is dephosphorylated at the tissue site by alkaline phosphatase to the metabolite, WR-1065. WR-1065 can be further oxidized to form both symmetrical and mixed disulfides, or undergo further metabolism via copper-dependent amine oxidase to form acrolein and cysteamine. To prevent further oxidation of WR-1065, PCA/EDTA was added to the samples prior to centrifugation. Because PCA/EDTA ruptures the cellular content of the blood, the samples were centrifuged for a longer period of time to prevent contamination/metabolism of the metabolite. Consequently, only the clear supernatant (serum) was used for analysis of WR-1065. In contrast, no PCA/EDTA was added to the blood samples designated for analysis of the parent drug; therefore, plasma samples were prepared for analysis of the parent drug.

6.9.3 Pharmacokinetic Analysis

Concentrations of amifostine (unchanged drug) and WR-1065 (metabolite) were measured using electrochemical-detection high-pressure liquid chromatography (HPLC)

methods as described by Shaw, et al. (Shaw et al. 1984, "A Liquid Chromatographic Electrochemical Assay for S-2-(3-Aminopropylamino) ethylphosphorothioate (WR-2721) in Human Plasma," *J. Liq. Chromatog.* 7:2447-2465; Shaw et al., 1986, "Measurement of S-2-(3-Aminopropyl Amino) ethanethiol (WR-1065) in Blood and Tissue," *J. Liq. Chromatog.* 9:845-859). WINNONLIN, the WINDOWS version of PCNONLIN, was used for the determination of pharmacokinetic parameters for each subject following each route of administration. Non-compartmental modelling of the data was performed.

6.10 Safety Assessments

All subjects who had received at least one dose of protocol therapy were considered evaluable for safety. Safety was evaluated during and after administration of amifostine (prior to subjects leaving the study site) via analyses of adverse events, physical examination and laboratory tests. Toxicity notation was done after each dose of amifostine. Toxicity was based on National Cancer Institute (NCI) Common Toxicity Criteria.

The following safety evaluations were done after the last dose of amifostine (on Day 3) but prior to subjects leaving the study site:

physical exam including vital signs (blood pressure, pulse and temperature);

CBC with differential and platelets;

blood chemistries including BUN, serum creatinine, calcium, total bilirubin, albumin, SGOT, SGPT, alkaline phosphatase, glucose and total protein;

urinalysis; and toxicity notation.

Subjects who had abnormal laboratory values at discharge had those parameters repeated. If the parameters remained abnormal, the subject was referred to a physician of his choice for follow-up.

6.11 Sample Size Determination

Using a 3×3 latin square method with 12 subjects, the power to detect a 30% difference in area under the curve (AUC) for amifostine (parent drug) and WR-1065 was 80%. This difference was defined as a change in AUC values (67% more or 40% less) for one route of administration versus the other two routes of administration. The power calculation assumed a standard deviation of 50% of the mean AUC and a 70% correction with subjects.

6.12 Statistical Analysis

The primary endpoint of this study was the relative bioavailability of 500 mg of amifostine administered orally or subcutaneously compared to 200 mg/m$^2$ of amifostine administered intravenously. As this was a crossover study in which each subject received amifostine by all three routes of administration, the bioavailabilities of subcutaneous and oral amifostine relative to intravenous amifostine were assessed within each subject.

Bioavailability was assessed using area under the plasma/serum concentration-time curve (AUC) from 0 to 4 hours. AUCs were calculated using extrapolation according to a straightline from the last non-zero point.

The bioavailability of amifostine (parent drug plus metabolite) following oral and subcutaneous administration was based on the ratio of AUCs of these routes of administration with the AUC of intravenous amifostine. The AUCs were then analyzed using an analysis of variance (ANOVA) model with route, period and subject as variables. Sequence was not included in the model as this variable was uniquely determined by route and period. The confidence interval on the ratio of the subcutaneous or oral route to the intravenous route was calculated using the mean square error from the entire ANOVA model.

Because this was a crossover study to be performed on three successive days, toxicities were assigned to the route of administration on the day the toxicity occurred. A full nonparametric crossover model (likelihood of ratio test) was used to assess toxicities which corrected for period and sequence effects. A PROC CATMOD of SAS@ was used for this analysis.

6.13 Results

Between Apr. 2, 1996 and Jul. 23, 1996, 12 healthy volunteers were enrolled onto this Phase I bioavailability study of amifostine given intravenously, orally and subcutaneously (Protocol WR-A057). This study was conducted at one site in the United States. All 12 subjects completed the study as per the protocol.

A total of 12 healthy men enrolled onto Protocol WR-A057 (TABLE 4). The median age of these subjects was 25.5 years, ranging from 18 to 34 years. The median body surface area (BSA) was 1.84 m$^2$, ranging from 1.69 to 2.15 m$^2$. All subjects had normal pretreatment laboratory values within 10% of the normal range and no vital sign abnormalities prior to receiving study medication. Moreover, all subjects had normal pretreatment EKG.

TABLE 4

Baseline Demographic Characteristics of the 12 Subjects Who Received Amifostine Intravenously, Orally and Subcutaneously

| Parameter | Number (n = 12) | Percent |
| --- | --- | --- |
| Age (years) | | |
| Median | 25.5 | |
| Range | 18-34 | |
| Race | | |
| Caucasian | A6 | (50.0%) |
| Black | 5 | (41.7%) |
| Other | 1 | (8.3%) |
| Body Surface Area (m$^2$) | | |
| Median | 1.84 | |
| Range | 1.69-2.15 | |
| Weight (kg) | | |
| Median | 70.2 | |
| Range | 59-91 | |
| Height (cm) | | |
| Median | 176.5 | |
| Range | 158-188 | |

6.13.1 Bioavailability

FIG. 1 shows the plasma/serum concentration-time curves for amifostine (parent drug plus metabolite) following oral, subcutaneous and intravenous administration of amifostine in all 12 subjects. As seen in this figure, the shape of the plasma/serum concentration-time curves of the three routes of administration were markedly different. Following a 200 mg/m$^2$ intravenous infusion (over 7.5 minutes), there was rapid uptake of amifostine within <1 minute of drug administration. Thereafter, plasma/serum concentrations of amifostine decreased rapidly. The maximum concentration of amifostine was approximately 130 µM 8 to 10 minutes after intravenous administration which dropped below 10 µM 45 minutes after drug administration.

Following a 500 mg subcutaneous injection, there was a markedly slower rise in plasma/serum concentrations of amifostine as compared to intravenous administration. The maximum concentration of amifostine (approximately 15 µM) was observed 15 minutes after subcutaneous administration and was maintained for approximately 30 minutes. Thereafter, concentrations of amifostine fell below 10 µM approximately 50 minutes after subcutaneous administration. Thirty minutes following administration of 200 mg/m² intravenous amifostine and 500 mg subcutaneous amifostine, the plasma/serum concentration-time curves of amifostine (parent drug plus metabolite) were identical.

Following oral administration (500 mg as an liquid formulation), the maximum concentration of amifostine (approximately 5 µM) was observed 5 to 8 minutes after drug administration. Concentrations of amifostine dropped below 1.0 µM at 10 to 13 minutes after oral drug administration. A second peak of approximately 4 µM was observed 45 minutes after oral drug administration which dropped to approximately 1 µM at 60 minutes after drug administration.

FIG. 2 shows the average plasma concentration-time curves for amifostine (parent drug) following oral, subcutaneous and intravenous administration of amifostine to the 12 subjects. There was no detectable amount of parent drug in plasma samples of subjects following oral amifostine. The shape of the plasma concentration-time curves of the intravenous and subcutaneous dose were similar to those seen in FIG. 1. Following the 200 mg/m² intravenous dose, there was rapid uptake of amifostine within <1 minute of drug administration. Thereafter, plasma concentrations of amifostine decreased rapidly. The maximum concentration of amifostine was approximately 100 µM 8 to 10 minutes after intravenous administration which dropped below 10 µM approximately 30 minutes after drug administration. Following a 500 mg subcutaneous injection, there was a slower rise in plasma concentrations of amifostine. The maximum concentration of amifostine (approximately 10 µM) was observed 15 minutes after subcutaneous and was maintained for approximately 30 minutes. Thereafter, concentrations of amifostine fell below 10 µM approximately 45 minutes after subcutaneous administration. Thirty minutes following administration of 200 mg/m² intravenous amifostine and 500 mg subcutaneous amifostine, the plasma concentration-time curves of the parent drug were similar but with higher concentrations of parent drug noted for subcutaneous amifostine versus intravenous amifostine.

FIG. 3 shows the average serum concentration-time curves for WR-1065 (metabolite) following subcutaneous, oral and intravenous administration of amifostine in all 12 subjects. As seen in this figure, the shape of the serum concentration-time curves of the three routes of administration were similar to those observed in FIG. 1. In fact, the serum concentration-time curve for oral amifostine in FIG. 1 was the exact same curve as in FIG. 3; this is due to the fact that there was no detectable amount of parent drug in the plasma samples of subjects following oral amifostine. Following a 200 mg/m² intravenous infusion, there was rapid uptake of WR-1065 within <1 minute of drug administration. Thereafter, serum concentrations of WR-1065 also decreased rapidly but at a slower rate than that which was observed with the parent drug (see FIG. 2). The maximum concentration of WR-1065 was approximately 30 µM 10 minutes after intravenous administration which fell below 5 µM approximately 45 minutes after drug administration. Following a 500 mg subcutaneous injection, there was a slower rise in serum concentrations of WR-1065. The maximum concentration of WR-1065 (approximately 5 µM) was observed 15 minutes after subcutaneous administration and was maintained for approximately 30 minutes. Thereafter, concentrations of WR-1065 fell below 5 µM approximately 60 minutes after subcutaneous administration. Forty minutes following administration of 200 mg/m² intravenous amifostine and 500 mg subcutaneous amifostine, the serum concentration-time curves of the metabolite were identical.

The primary endpoint of this study was the relative bioavailability of 500 mg amifostine administered orally or subcutaneously to 200 mg/m² amifostine administered intravenously. TABLE 5 lists the AUC values of amifostine (parent drug and metabolite combined) for each subject following oral, subcutaneous and intravenous administration of amifostine. Based on the ratio of AUCs, the relative bioavailability of amifostine (parent drug and metabolite) following a 500 mg subcutaneous dose was 0.67 (95% confidence interval of 0.37 to 0.98) of the 200 mg/m² intravenous dose. The relative bioavailability of amifostine following a 500 mg oral dose was 0.11 (95% confidence interval of 0.04 to 0.18) of the 200 mg/m² intravenous dose.

TABLE 5

Relative Bioavailability of 500 mg Amifostine Administered Orally or Subcutaneously to 200 mg/m² Amifostine Administered Intravenously in 12 Healthy, Male Subjects(Parent Drug and Metabolite Combined)

| | AUC (µM × min) of Combined | | | Bioavailability | |
|---|---|---|---|---|---|
| | 500 mg | 500 mg | 200 mg/m² | | |
| Subject Number | Subcutaneous (SC) | Oral (PO) | Intravenous (IV) | Ratio PO/IV | Ratio SC/IV |
| 1001 | 1726 | 656 | 1573 | 0.42 | 1.10 |
| 1002 | 2411 | 243 | 2820 | 0.09 | 0.86 |
| 1003 | 3946 | 456 | 2432 | 0.19 | 1.62 |
| 1004 | 475 | 131 | 2198 | 0.06 | 0.22 |
| 1005 | 643 | 378 | 1383 | 0.27 | 0.46 |
| 1006 | 180 | 132 | 1876 | 0.07 | 0.10 |
| 1007 | 732 | 50 | 2102 | 0.02 | 0.35 |
| 1008 | 3080 | 42 | 1811 | 0.02 | 1.70 |
| 1009 | 550 | 86 | 1296 | 0.07 | 0.42 |
| 1010 | 348 | 0 | 1343 | 0.00 | 0.26 |
| 1011 | 985 | 121 | 1382 | 0.09 | 0.71 |
| 1012 | 550 | 2 | 1832 | 0.00 | 0.30 |
| Mean | 1302 | 191 | 1837 | 0.11 | 0.67 |
| 95% CI* | 611-1993 | 75-307 | 1565-2109 | 0.04-0.18 | 0.37-0.98 |

CI: confidence interval.
*Using the mean square error from the ANOVA model.

TABLE 6 lists the AUC values of the parent drug for each subject following oral, subcutaneous and intravenous administration of amifostine. Based on the ratio of AUCs, the relative bioavailability of the parent drug following a 500 mg subcutaneous dose was 0.72 (95% confidence interval of 0.26 to 1.18) of the 200 mg/m² intravenous dose. The relative bioavailability of the parent drug following a 500 mg oral dose was 0.00 as no parent drug was detected in blood samples of subjects following oral administration of amifostine (see FIG. 2).

TABLE 6

Relative Bioavailability of 500 mg Amifostine Administered Orally or Subcutaneously to 200 mg/m² Amifostine Administered Intravenously in 12 Healthy, Male Subjects
(Parent Drug)

| | AUC (µM × min) of Parent Drug | | | Bioavailability | |
|---|---|---|---|---|---|
| Subject Number | 500 mg Subcutaneous (SC) | 500 mg Oral (PO) | 200 mg/m² Intravenous (IV) | Ratio PO/IV | Ratio SC/IV |
| 1001 | 1208 | 0 | 840 | 0.00 | 1.44 |
| 1002 | 1135 | 0 | 1305 | 0.00 | 0.87 |
| 1003 | 2883 | 0 | 1238 | 0.00 | 2.33 |
| 1004 | 224 | 0 | 1759 | 0.00 | 0.13 |
| 1005 | 305 | 0 | 805 | 0.00 | 0.38 |
| 1006 | 0 | 0 | 1526 | 0.00 | 0.00 |
| 1007 | 515 | 0 | 1723 | 0.00 | 0.30 |
| 1008 | 2924 | 0 | 1378 | 0.00 | 2.12 |
| 1009 | 154 | 0 | 812 | 0.00 | 0.19 |
| 1010 | 264 | 0 | 928 | 0.00 | 0.28 |
| 1011 | 697 | 0 | 1156 | 0.00 | 0.60 |
| 1012 | 0 | 0 | 1351 | 0.00 | 0.00 |
| Mean | 859 | 0 | 1235 | 0.00 | 0.72 |
| 95% CI* | 274-1444 | — | 1044-1426 | — | 0.26-1.18 |

CI: confidence interval.
*Using the mean square error from the ANOVA model.

TABLE 7 lists the AUC values of the metabolite (WR-1065) for each subject following oral, subcutaneous and intravenous administration of amifostine. Based on the ratio of AUCs, the relative bioavailability of the metabolite following a 500 mg subcutaneous dose was 0.71 (95% confidence interval of 0.55 to 0.86) of the 200 mg/m² intravenous dose. The relative bioavailability of the metabolite following a 500 mg oral dose was 0.32 (95% confidence interval of 0.16 to 0.48) of the 200 mg/m² intravenous dose.

TABLE 7

Relative Bioavailability of 500 mg Amifostine Administered Orally or Subcutaneously to 200 mg/m² Amifostine Administered Intravenously in 12 Healthy, Male Subjects
(Metabolite)

| | AUC (µM × min) of Metabolite | | | Bioavailability | |
|---|---|---|---|---|---|
| Subject Number | 500 mg Subcutaneous (SC) | 500 mg Oral (PO) | 200 mg/m² Intravenous (IV) | Ratio PO/IV | Ratio SC/IV |
| 1001 | 518 | 656 | 745 | 0.88 | 0.70 |
| 1002 | 1587 | 243 | 1583 | 0.15 | 1.00 |
| 1003 | 1047 | 456 | 1234 | 0.37 | 0.85 |
| 1004 | 251 | 131 | 424 | 0.31 | 0.59 |
| 1005 | 338 | 378 | 569 | 0.66 | 0.59 |
| 1006 | 180 | 132 | 265 | 0.50 | 0.68 |
| 1007 | 218 | 50 | 381 | 0.13 | 0.57 |
| 1008 | 142 | 42 | 437 | 0.10 | 0.32 |
| 1009 | 379 | 86 | 482 | 0.18 | 0.79 |
| 1010 | 84 | 0 | 338 | 0.00 | 0.25 |
| 1011 | 188 | 121 | 203 | 0.59 | 0.93 |
| 1012 | 550 | 2 | 457 | 0.00 | 1.20 |
| Mean | 457 | 191 | 593 | 0.32 | 0.71 |
| 95% CI* | 207-707 | 75-307 | 360-826 | 0.16-0.48 | 0.55-0.86 |

CI: confidence interval.
*Using the mean square error from the ANOVA model.

The aforementioned AUC data presented in TABLES 5, 6 and 7 were used to calculate the absolute bioavailability of amifostine following oral and subcutaneous administration. Using the 200 mg/m² intravenous dose as the dose representing 100% bioavailability, the AUC data for oral and subcutaneous amifostine were adjusted for dose and compared with the AUC data for intravenous amifostine. Based on the ratio of AUCs, in contrast to the relative bioavailabilities, the absolute bioavailability of amifostine (parent drug plus metabolite) following subcutaneous administration was 0.50 (95% confidence interval of 0.27 to 0.73) of the intravenous dose. The absolute bioavailabilities of the parent drug and the metabolite following subcutaneous administration were 0.53 (95% confidence interval of 0.18 to 0.88) and 0.53, respectively, (95% confidence interval of 0.41 to 0.64) of the intravenous dose. The absolute bioavailability of amifostine (parent drug plus metabolite) following oral administration was 0.08 (95% confidence interval of 0.03 to 0.13) of the intravenous dose.

6.13.2 Efficacy

Plasma concentrations of amifostine (parent drug) and serum concentrations of WR-1065 (metabolite) were measured in blood samples obtained from 12 healthy, male subjects prior to and up to 4 hours after receiving amifostine as a 500 mg subcutaneous injection, a 500 mg oral solution and a 200 mg/m² intravenous infusion (over 7.5 minutes). From these data, plasma/serum concentration-time curves were generated and used to determine the pharmacokinetic profile of amifostine (both parent drug and metabolite) following each route of administration.

As shown in FIG. 1, the shapes of the plasma/serum concentration-time curves for amifostine (parent drug plus metabolite) of the three routes of administration were different. Following all three routes of administration, there was rapid uptake of amifostine within 5 minutes of drug administration. The intravenous route exhibited the fastest rate of uptake, followed by the subcutaneous route and the oral route. There after, plasma/serum concentrations of amifostine declined. The rate of decline was fastest for the intravenous route and slowest for the subcutaneous route. The maximum concentration of amifostine (parent drug plus metabolite) following intravenous administration was approximately 130 µM (approximately 100 µM for parent drug and 30 µM for metabolite). Maximum concentrations of amifostine (parent plus metabolite) after subcutaneous and oral administration were approximately 15 µM and 5 µM, respectively. Maximum concentrations were reached at approximately 15 minutes and plateaued until approximately 45 minutes of drug administration. As shown in FIG. 2, there was no detectable amount of parent drug in plasma samples of subjects following oral amifostine.

6.13.3 Adverse Events

TABLE 8 lists those subjects who reported an adverse event following intravenous, oral and subcutaneous administration of amifostine. No subject discontinued amifostine due to adverse events. All adverse events were mild in severity, transient and considered related to amifostine. Five subjects reported adverse events following intravenous amifostine versus one subject each following oral and subcutaneous amifostine. Nausea was the most common adverse event. Other adverse events included headache, hypotension, vomiting, lightheadedness and somnolence.

TABLE 8

List of Subjects Who Reported Adverse Events* Following Intravenous, Oral and Subcutaneous Administration of Amifostine (N = 12)

| Adverse Event | Intravenous | Oral | Subcutaneous |
|---|---|---|---|
| Headache | 1008 | | |
| Hypotension | 1003 | 1003 | |
| Nausea | 1001, 1003, 1005, 1007, 1008 | | 1002 |
| Vomiting | 1008 | | |
| Lightheadedness | 1003 | 1003 | |
| Somnolence | 1008 | | |

*All adverse events were mild in severity and related to amifostine.

6.13.3.1 Hypotension

Mild and transient episodes of hypotension were reported by one subject after intravenous and oral administration of amifostine (TABLE 10). On Day 2 of the study, Subject 1003 had a pre-infusion blood pressure reading of 115/58 mm Hg which decreased to 99/56 mm Hg, 5 minutes after completion of the infusion. Five minutes later, his blood pressure returned to baseline (114/56 mm Hg). Subject 1003 also experienced two episodes of hypotension following oral administration of amifostine on Day 3. With a baseline blood pressure reading of 121/70 mm Hg, transient decreases in blood pressure (99/49 and 98/51 mm Hg) were observed at 5 and 25 minutes after oral administration of amifostine, respectively. Thereafter, none of the other blood pressure readings met the criteria for hypotension.

There was no incidence of hypotension following subcutaneous administration of amifostine.

6.13.3.2 Emesis

Six subjects reported nausea and one subject vomited during the study. Nausea was reported in five subjects following intravenous amifostine and in one subject following subcutaneous amifostine (TABLE 10). Vomiting was reported in one subject following intravenous amifostine. All episodes of nausea/vomiting were mild in severity and transient in nature. Antiemetic therapy was prescribed in two subjects following intravenous amifostine. Subject 1007 received prochlorperazine (10 mg) for nausea, and Subject 1008 received prochlorperazine (10 mg) for nausea/vomiting.

6.13.3.3 Clinical Evaluations

Physical examinations including weight and vital signs (blood pressure, pulse and temperature) were performed after the last dose of amifostine but prior to subjects leaving the study site. No remarkable changes were noted in these parameters following the last dose of amifostine.

6.13.3.4 Clinical Laboratory Tests

Laboratory tests including hematology, serum chemistry and urinalysis were performed after the last dose of amifostine but prior to subjects leaving the study site. Laboratory results were compared to laboratory reference ranges as well as to NCI Common Toxicity Criteria. One subject (Subject 1010) had a serum creatinine value (0.60 mg/dL)>10% below the lower limit of the reference range (0.70 to 1.40 mg/dL); his baseline value was 0.90 mg/dL. This low value was considered by the inventors as clinically insignificant. In addition, none of the subjects experienced a Grade 2 or higher laboratory toxicity according to NCI Common Toxicity Criteria.

6.13.3.5 Safety Conclusions

Amifostine was well tolerated regardless of route of administration. All 12 subjects completed the required study medication as per the protocol. No subject discontinued amifostine due to adverse events. All adverse events were mild in severity, transient and considered related to amifostine. Five subjects reported adverse events following intravenous amifostine versus one subject each following oral and subcutaneous amifostine (TABLE 8). Nausea was the most common adverse event. Other adverse events included headache, hypotension, vomiting, lightheadedness and somnolence. Mild and transient episodes of hypotension were reported by one subject after intravenous and oral administration of amifostine. These episodes occurred after amifostine administration, and none lasted more than 5 minutes in duration. There was no incidence of hypotension following subcutaneous administration of amifostine. There were no remarkable findings for any of the clinical evaluations or clinical laboratory tests.

7. EXAMPLE

Subcutaneous Administration of Amifostine Protected Animals Against Radiation-Induced Mucositis One of the major limiting acute toxicities associated with radiotherapy is radiation-induced mucositis. The ability to reduce the duration and severity of acute mucosal reactions is of particular importance in the radiotherapy and/or chemotherapy of head and neck cancer. Therefore, the radioprotective effects of amifostine were examined in an experimental model of mucositis. In particular, the study compared the radioprotective effects of amifostine by subcutaneous (s.c.) and intraperitoneal (i.p.) administration. The mouse model developed by Parkins et al. was used to examine the mucosal reactions in the inferior lip of mice after irradiation, and this model has been established as a reproducible model in the art (Parkins et al., 1983, Radiother. Oncol. 1:159-165).

7.1 Experimental Design

C57BL/6 female mice of 8-10 weeks old were used and fed with semi liquid food. A total of 40 mice were randomly divided into eight treatment groups of five mice each. The treatment groups were:

Group 1: Saline solution (i.p.) and irradiation
Group 2: Saline solution (s.c.) and irradiation
Group 3: Amifostine (200 mg/Kg, i.p.) and irradiation
Group 4: Amifostine (400 mg/Kg, i.p.) and irradiation
Group 5: Amifostine (200 mg/Kg, s.c.) and irradiation
Group 6: Amifostine (400 mg/Kg, s.c.) and irradiation
Group 7: Saline solution (i.p.)
Group 8: Saline solution (s.c.)

Unanesthetized mice were maintained in supine position and irradiated exclusively on the tip of their mouth. They were immobilized using jigs comparable to those previously used by Ang et al. (1982, Int. J. Radiat. Oncol. Biol. Phys. 8:145-148). Irradiation was performed with a RT 250 Philips apparatus delivering 1.98 Gy per min. (200 Kv, 20 mA, filter of 0.2 mm de Cu). During irradiation, a constant normobaric air renewal was maintained. The effects of amifostine were evaluated using a single dose of 16.5 Gy.

7.2 Administration of Amifostine

Amifostine was dissolved in physiological saline (0.9% Nacl to achieve a final concentration of 50 mg/ml) immediately before injections at 200 or 400 mg/Kg body weight. Both i.p. and s.c. injections were conducted 30 minutes before irradiation. A placebo solution of saline alone was used for the control group.

7.3 Mucositis Scoring System

The effects of irradiation on lip mucosa were evaluated using the scoring system described by Parkins et al. (1983, Radiother. Oncol. 1:159-165). Body weight of the treated mice were scored daily after treatment. Reduction in body weight was used as an objective indication of the severity of mucositis induced by irradiation, presumably resulting from the inability of the animals to eat. In this model, the acute reactions peaked around day 10 to 11 after irradiation.

Other symptoms of mucositis such as mucosal erythema and edema were also recorded. These symptoms developed more slowly than weight loss following irradiation. Mucosal erythema and edema were scored separately, and could be analyzed as separate scores or as a combined score yielding a maximum score of 7. Mouse lip mucosal erythema was scored according to Table 9.

TABLE 9

Scoring System for Mucosal Erythema

| Score | Mucosal Observation |
|---|---|
| 0.5 | doubtful if abnormally pink |
| 1 | slight but definitely reddening |
| 2 | severe reddening |
| 3 | focal desquamation |
| 4 | exudation or crusting covering about ½ lip area |
| 5 | exudation or crusting covering more than ½ lip area |

Mucosal edema (swelling) of the lips was scored according to Table 10.

TABLE 10

Scoring System for Mucosal Edema

| Score | Mucosal Observation |
|---|---|
| 0.5 | 50-50 doubtful if any swelling |
| 1 | slight but definitely swelling |
| 2 | sever swelling |

7.4 Results

Body weight reduction of irradiated mice was measured as an objective indicator of mucositis (Table 11). A single dose of irradiation greatly reduced the body weight of the animals, particularly 7-13 days after treatment (FIGS. 4A and 4B). Non-irradiated animals maintained steady body weight throughout the course of the study. Reduction in body weight was prevented in animals which received either i.p. or s.c. injection of amifostine. The radioprotective effects of amifostine were dose dependent.

Non-irradiated mice had no erythema during the entire period of the experiment (Table 12). In contrast, erythema was observed in all irradiation groups (FIGS. 5A and 5B). Both i.p and s.c. administration of amifostine decreased the average erythema score as compared to saline plus irradiation. Similarly, mucosal edema scores were decreased by both injection methods of amifostine (FIGS. 6A and 6B, Table 13).

The data presented in FIGS. 4A, 4B, 5A, 5B, 6A, 6B and Tables 11-13 show that both s.c. and i.p. administration were effective in reducing the adverse effects of radiation, as measured by three mucositis indicators, i.e., body weight, erythema score and edema score. Furthermore, the subcutaneous administration of amifostine at 200 mg/kg produced the highest efficacy at the time points of maximal adverse effects (i.e., day 9 for body weight and day 12 for erythema and edema). An increase in the dose of amifostine from 200 mg/kg to 400 mg/kg produced minimal additional benefits. Thus, these results indicate that subcutaneously administered amifostine may have improved efficacy over other routes of administration, such as i.p.

TABLE 11

| | | Body Weight | | | | | |
|---|---|---|---|---|---|---|---|
| | 0 | 6 | 7 | 9 | 12 | 13 | 14 |
| | | Saline (l.p.) + Irradiation | | | | | |
| Days | | | | | | | |
| 1 | 20 | 19.8 | 16.3 | 16.5 | 15.1 | 15.5 | 18.4 |
| 2 | 20 | 17.4 | 14.6 | 13.3 | 14.3 | 13.87 | 15.4 |
| 3 | 20 | 17.8 | 16 | 13.9 | 14.8 | 15.6 | 16.9 |
| 4 | 19.5 | 16.8 | 15.6 | 13.7 | 15.2 | 16.4 | 17.9 |
| 5 | 19 | 18.2 | 16.1 | 15.4 | 15.1 | 14 | 16.8 |
| Mean | 19.7 | 18 | 15.72 | 14.56 | 14.9 | 15.074 | 17.08 |
| Standard | 0.2 | 0.505964 | 0.302324 | 0.601332 | 0.164317 | 0.490893 | 0.517107 |
| | | Saline (s.c.) + Irradiation | | | | | |
| Mouse | | | | | | | |
| 1 | 20 | 20.1 | 18.8 | 18 | 17.6 | 18.46 | 20.9 |
| 2 | 20 | 17.8 | 15.5 | 14.5 | 15.7 | 16 | 18.2 |
| 3 | 20 | 19 | 18.1 | 17.1 | 16.9 | 18.5 | 20.2 |
| 4 | 21 | 19 | 17.7 | 16.4 | 17.7 | 19 | 21.5 |
| 5 | 20 | 18.2 | 15.7 | 14.4 | 16.6 | 17.5 | 18.8 |
| Mean | 20.2 | 18.82 | 17.16 | 16.08 | 16.9 | 17.892 | 19.92 |
| Standard | 0.2 | 0.395474 | 0.661513 | 0.71232 | 0.364692 | 0.531662 | 0.622415 |
| | | Amifostine (l.p.) at 200 mg/kg + Irradiation | | | | | |
| 1 | 20 | 18.1 | 19.1 | 18 | 19.3 | 19.3 | 19.8 |
| 2 | 20 | 18.1 | 16.7 | 17 | 19.7 | 19.6 | 20.1 |
| 3 | 20 | 18.6 | 18.3 | 17.3 | 19.3 | 19.4 | 20 |
| 4 | 20 | 19 | 19.6 | 20.1 | 21.3 | 21.4 | 21.6 |
| 5 | 20 | 20 | 20.7 | 20.4 | 21.3 | 21 | 21 |
| Mean | 20 | 18.76 | 18.88 | 18.56 | 20.18 | 20.14 | 20.5 |
| Standard | 0 | 0.352987 | 0.669627 | 0.710352 | 0.463033 | 0.44 | 0.343511 |

TABLE 11-continued

| | Body Weight | | | | | | |
|---|---|---|---|---|---|---|---|
| | 0 | 6 | 7 | 9 | 12 | 13 | 14 |
| Amifostine (I.p.) at 400 mg/kg + Irradiation | | | | | | | |
| 1 | 20.5 | 19.7 | 20 | 20.4 | 21.2 | 20.8 | 21.6 |
| 2 | 19 | 18.1 | 19.4 | 18.2 | 18.7 | 19 | 18.8 |
| 3 | 21 | 19.2 | 20.7 | 21.8 | 21 | 21.3 | 21.8 |
| 4 | 19 | 19.4 | 20.4 | 20.8 | 20.8 | 21.2 | 21.1 |
| Mean | 19.875 | 19.1 | 20.125 | 20.3 | 20.425 | 20.575 | 20.825 |
| Standard | 0.515388 | 0.348807 | 0.280995 | 0.759386 | 0.580768 | 0.535996 | 0.690863 |
| Amifostine (s.c.) at 200 mg/kg + Irradiation | | | | | | | |
| 1 | 20 | 17.7 | 18.3 | 19.4 | 18.6 | 19.2 | 19.8 |
| 2 | 20 | 18.8 | 19.9 | 20.6 | 19.5 | 19.8 | 20.9 |
| 3 | 19.5 | 18.2 | 19.3 | 19.6 | 19.5 | 19.7 | 20.2 |
| 4 | 19 | 18.7 | 19 | 19.5 | 20.3 | 20.3 | 22.2 |
| 5 | 19 | 18.9 | 18.8 | 19.8 | 19.9 | 20 | 21.5 |
| Mean | 19.5 | 18.46 | 19.06 | 19.78 | 19.56 | 19.8 | 20.92 |
| Standard | 0.223607 | 0.224944 | 0.265707 | 0.215407 | 0.282135 | 0.181659 | 0.432897 |
| Amifostine (s.c.) at 400 mg/kg + Irradiation | | | | | | | |
| 1 | 20 | 19 | 19.4 | 20.6 | 19.9 | 20.5 | 21.4 |
| 2 | 20 | 19.7 | 19.8 | 20.8 | 18.8 | 20.3 | 21 |
| 3 | 19.5 | 20 | 20.6 | 21.4 | 20.7 | 21.1 | 21.4 |
| 4 | 21 | 16.9 | 19.2 | 20.7 | 21.7 | 22 | 24 |
| 5 | 20 | 19.6 | 20 | 20.7 | 20.8 | 21.3 | 21.7 |
| Mean | 20.1 | 19.04 | 19.8 | 20.84 | 20.38 | 21.04 | 21.9 |
| Standard | 0.244949 | 0.559106 | 0.244949 | 0.143527 | 0.487237 | 0.302655 | 0.536656 |
| Saline (I.p.) | | | | | | | |
| 1 | 20 | 20.7 | 19.8 | 20.4 | 19.9 | 20.7 | 20.9 |
| 2 | 19.3 | 19.6 | 19.1 | 20.5 | 20.1 | 19.9 | 20.5 |
| 3 | 20.6 | 21.1 | 21.1 | 21.5 | 21.5 | 21.5 | 23.1 |
| 4 | 19.3 | 20.2 | 20.1 | 20.3 | 20.6 | 21.2 | 21.1 |
| 5 | 21 | 20.1 | 21 | 21.8 | 21.1 | 21.6 | 21.6 |
| Mean | 20.04 | 20.34 | 20.22 | 20.9 | 20.64 | 20.98 | 21.44 |
| Standard | 0.341467 | 0.25807 | 0.376032 | 0.311448 | 0.299333 | 0.31209 | 0.451221 |
| Saline (s.c.) | | | | | | | |
| 1 | 20 | 19.8 | 19.7 | 20.7 | 20 | 20.7 | 21.5 |
| 2 | 19.3 | 19.2 | 19.4 | 20.1 | 19.8 | 20.3 | 20.9 |
| 3 | 20.5 | 20 | 20.4 | 21 | 20.1 | 21 | 21.6 |
| 4 | 20.2 | 20.1 | 20.3 | 21 | 20.2 | 20.8 | 21.3 |
| 5 | 20 | 20.2 | 20.2 | 21.1 | 20.8 | 21.4 | 22.6 |
| 6 | 19 | 19.2 | 19.2 | 20.1 | 19.6 | 20.2 | 20.9 |
| Mean | 19.83333 | 19.75 | 19.86667 | 20.66667 | 20.08333 | 20.73333 | 21.46667 |
| Standard | 0.2319 | 0.182117 | 0.20602 | 0.18738 | 0.16816 | 0.181965 | 0.256472 |

TABLE 12

| | Erythema | | | | | |
|---|---|---|---|---|---|---|
| | Days after treatment | | | | | |
| Mouse | 6 | 7 | 9 | 12 | 13 | 14 |
| Saline (I.p.) + Irradiation | | | | | | |
| 1 | 0.5 | 0 | 2 | 5 | 2 | 2 |
| 2 | 0 | 0.5 | 4 | 4 | 3 | 3 |
| 3 | 0.5 | 0.5 | 4 | 5 | 5 | 4 |
| 4 | 0.5 | 0.5 | 1 | 5 | 2 | 3 |
| 5 | 0 | 0.5 | 2 | 5 | 3 | 2 |
| Mean | 0.3 | 0.4 | 2.6 | 4.8 | 3 | 2.8 |
| Standard | 0.122474 | 0.1 | | 0.6 | 0.2 | 0.547723 | 0.374166 |
| Saline (s.c.) + Irradiation | | | | | | |
| 1 | 0 | 0.5 | 2 | 4 | 3 | 2 |
| 2 | 0 | 0.5 | 2 | 5 | 3 | 3 |
| 3 | 0 | 0 | 2 | 5 | 5 | 3 |
| 4 | 0 | 0 | 2 | 4 | 2 | 2 |
| 5 | 0 | 0.5 | 1 | 3 | 2 | 2 |
| Mean | 0 | 0.3 | 1.8 | 4.2 | 3 | 2.4 |
| Standard | 0 | 0.122474 | 0.2 | 0.374166 | 0.547723 | 0.244949 |

TABLE 12-continued

Erythema
Days after treatment

| Mouse | 6 | 7 | 9 | 12 | 13 | 14 |
|---|---|---|---|---|---|---|
| Amifostine (I.p.) at 200 mg/kg + Irradiation | | | | | | |
| 1 | 0.5 | 0.5 | 1 | 4 | 0.5 | 0.5 |
| 2 | 0 | 0 | 2 | 4 | 2 | 2 |
| 3 | 0 | 0 | 1 | 3 | 2 | 1 |
| 4 | 0.5 | 0.5 | 1 | 3 | 1 | 0 |
| 5 | 0 | 0 | 1 | 1 | 0.5 | 0 |
| Mean | 0.2 | 0.3 | 1.2 | 3 | 1.2 | 0.7 |
| Standard | 0.122474 | 0.122474 | 0.2 | 0.547723 | 0.339116 | 0.374166 |
| Amifostine (I.p.) at 400 mg/kg + Irradiation | | | | | | |
| 1 | 0 | 0 | 0.5 | 3 | 0 | 0 |
| 2 | 0 | 0 | 1 | 1 | 0.5 | 0.5 |
| 3 | 0 | 0 | 0.5 | 1 | 0.5 | 0 |
| 4 | 0 | 0 | 1 | 2 | 0 | 0 |
| Mean | 0 | 0 | 0.75 | 1.75 | 0.25 | 0.125 |
| Standard | 0 | 0 | 0.144338 | 0.478714 | 0.144338 | 0.125 |
| Amifostine (s.c.) at 200 mg/kg + Irradiation | | | | | | |
| 1 | 0 | 0 | 0.5 | 2 | 1 | 0.5 |
| 2 | 0 | 0 | 1 | 2 | 0.5 | 0.5 |
| 3 | 0 | 0.5 | 1 | 1 | 2 | 0.5 |
| 4 | 0 | 0 | 3 | 2 | 1 | 0.5 |
| 5 | 0 | 0 | 3 | 3 | 1 | 1 |
| Mean | 0 | 0.1 | 1.7 | 2 | 1.1 | 0.6 |
| Standard | 0 | 0.1 | 0.538516 | 0.316228 | 0.244949 | 0.1 |
| Amifostine (s.c.) at 400 mg/kg + Irradiation | | | | | | |
| 1 | 0 | 0 | 2 | 3 | 1 | 1 |
| 2 | 0 | 0 | 1 | 1 | 0 | 0 |
| 3 | 0 | 0 | 2 | 1 | 0.5 | 0 |
| 4 | 0 | 0 | 2 | 3 | 1 | 0 |
| 5 | 0 | 0 | 1 | 2 | 1 | 0.5 |
| Mean | 0 | 0 | 1.6 | 2 | 0.7 | 0.3 |
| Standard | 0 | 0 | 0.244949 | 0.447214 | 0.2 | 0.2 |
| Saline (l.p.) | | | | | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| Mean | 0 | 0 | 0 | 0 | 0 | 0 |
| Standard | 0 | 0 | 0 | 0 | 0 | 0 |
| Saline (s.c.) | | | | | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| 6 | 0 | 0 | 0 | 0 | 0 | 0 |
| Mean | 0 | 0 | 0 | 0 | 0 | 0 |
| Standard | 0 | 0 | 0 | 0 | 0 | 0 |

TABLE 13

Oedema
Days after treatment

| Mouse | 6 | 7 | 9 | 12 | 13 | 14 |
|---|---|---|---|---|---|---|
| Saline (l.p.) + Irradiation | | | | | | |
| 1 | 0.5 | 0.5 | 1 | 2 | 2 | 1 |
| 2 | 0 | 0.5 | 0.5 | 2 | 2 | 2 |
| 3 | 0.5 | 0.5 | 2 | 2 | 2 | 2 |
| 4 | 0.5 | 0.5 | 1 | 2 | 2 | 2 |
| 5 | 0.5 | 0.5 | 2 | 2 | 2 | 7 |
| Mean | 0.4 | 0.5 | 1.3 | 2 | 2 | 2.8 |
| Standard | 0.1 | 0 | 0.3 | 0 | 0 | 1.067708 |

TABLE 13-continued

Oedema
Days after treatment

Saline (s.c.) + Irradiation

| Mouse | 6 | 9 | 12 | 13 | 14 |
|---|---|---|---|---|---|
| 1 | 0 | 1 | 2 | 2 | 1 |
| 2 | 0.5 | 1 | 2 | 2 | 2 |
| 3 | 0.5 | 0.5 | 2 | 2 | 1 |
| 4 | 0.5 | 1 | 2 | 2 | 1 |
| 5 | 0.5 | 2 | 2 | 2 | 2 |
| Mean | 0.4 | 1.1 | 2 | 2 | 1.4 |
| Standard | 0.1 | 0.244949 | 0 | 0 | 0.244949 |

| Mouse | 6 | 7 | 9 | 12 | 13 | 14 |
|---|---|---|---|---|---|---|
| Amifostine (l.p.) at 200 mg/kg + Irradiation | | | | | | |
| 1 | 1 | 1 | 1 | 2 | 0.5 | 0.5 |
| 2 | 0 | 0 | 1 | 2 | 2 | 2 |
| 3 | 0.5 | 0.5 | 1 | 2 | 2 | 1 |
| 4 | 0.5 | 0.5 | 0.5 | 1 | 1 | 0.5 |
| 5 | 0 | 0 | 0.5 | 0.5 | 0.5 | 0 |
| Mean | 0.4 | 0.4 | 0.8 | 1.5 | 1.2 | 0.8 |
| Standard | 0.187083 | 0.187083 | 0.122474 | 0.316228 | 0.339116 | 0.339116 |
| Amifostine (l.p.) at 400 mg/kg + Irradiation | | | | | | |
| 1 | 0.5 | 0.5 | 0.5 | 1 | 0.5 | 0.5 |
| 2 | 0 | 0 | 0.5 | 0.5 | 0.5 | 0.5 |
| 3 | 0.5 | 0.5 | 0.5 | 0.5 | 0 | 0 |
| 4 | 0 | 0.5 | 0.5 | 1 | 0.5 | 0.5 |
| Mean | 0.25 | 0.375 | 0.5 | 0.75 | 0.375 | 0.375 |
| Standard | 0.144338 | 0.125 | 0 | 0.144338 | 0.125 | 0.125 |
| Amifostine (s.c.) at 200 mg/kg + Irradiation | | | | | | |
| 1 | 0.5 | 0.5 | 0.5 | 1 | 0.5 | 0.5 |
| 2 | 1 | 0.5 | 1 | 1 | 1 | 1 |
| 3 | 0.5 | 0.5 | 1 | 0.5 | 1 | 0.5 |
| 4 | 0.5 | 0.5 | 1 | 1 | 1 | 0 |
| 5 | 0.5 | 0.5 | 2 | 1 | 1 | 1 |
| Mean | 0.6 | 0.5 | 1.1 | 0.9 | 0.9 | 0.6 |
| Standard | 0.1 | 0 | 0.244949 | 0.1 | 0.1 | 0.187083 |
| Amifostine (s.c.) at 400 mg/kg + Irradiation | | | | | | |
| 1 | 1 | 0.5 | 1 | 0.5 | 0.5 | 1 |
| 2 | 0.5 | 0.5 | 0.5 | 0.5 | 0.5 | 0 |
| 3 | 0.5 | 0 | 1 | 0.5 | 0.5 | 0.5 |
| 4 | 1 | 0.5 | 1 | 1 | 1 | 0.5 |
| 5 | 0 | 0.5 | 1 | 1 | 1 | 0.5 |
| Mean | 0.6 | 0.4 | 0.9 | 0.7 | 0.7 | 0.5 |
| Standard | 0.187083 | 0.1 | 0.1 | 0.122474 | 0.122474 | 0.158114 |
| Saline (l.p.) | | | | | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| Mean | 0 | 0 | 0 | 0 | 0 | 0 |
| Standard | 0 | 0 | 0 | 0 | 0 | 0 |
| Saline (s.c.) | | | | | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| 6 | 0 | 0 | 0 | 0 | 0 | 0 |
| Mean | 0 | 0 | 0 | 0 | 0 | 0 |
| Standard | 0 | 0 | 0 | 0 | 0 | 0 |

8. EXAMPLE

Subcutaneous Administration of Amifostine Stimulated Bone Marrow Cell Growth in Humans

8.1 Subcutaneous Administration of Amifostine in MDS Patients

All patients in the study had MDS and were diagnosed as having one of the following subtypes: refractory anemia, refractory anemia with ring sideroblasts, refractory anemia with excess blasts or refractory anemia with excess blasts in transformation. In addition, the patients had thrombocytopenia (platelets <100,000/μl), neutropenia (ANC or absolute neutrophil count<1500/μl) or a hemoglobin untransfused <10 g/dl and/or were transfusion-dependent as defined by requiring at least 4 units of RBC in the 10 weeks prior to entry. They had not received any previous treatment other than transfusion for MDS within 30 days prior to the study.

A 500 mg vial of amifostine was dissolved in 2.5 ml of 0.9% NaCl for s.c. administration. If the calculated dose of amifostine required more than 2 ml volume for dissolution, a total volume was evenly divided and administered as two s.c. injections. Blood pressure was monitored before treatment and after the first dose at 30 minute intervals for up to 90 minutes. A single dose of amifostine was given at 500 mg. At least three patients were treated with each dose. For one cycle of treatment, the patients were given amifostine once/day Mondays through Fridays for three weeks, followed by two weeks of rest. Hematologic responses to treatment were evaluated by measuring neutrophil count (ANC), platelet count, erythroid response including hemoglobin levels and reticulocyte count, and in vitro colony formation.

8.2 Results

Among the patients who received s.c. administration of amifostine, 17 patients were evaluated for hematologic responses. Among the 17 evaluated patients, 4 previously received amifostine intravenously prior to the study. The patients had diverse cytogenetic patterns with 8 patients showing normal karyotype and 9 patients showing abnormal karyotype. Minimal adverse effects were observed in the treated patients: nausea (grade I/II) in one patient, fatigue (grade I/II) in four patients, rash (grade I/II) in six patients, vomiting (grade I/II) in one patient, local reaction (grade III) in one patient and metallic taste (grade I/II) in one patient.

Table 14 shows that 29% of the treated patients showed 50% or greater increase of ANC as compared to pre-treatment levels. In addition, 33% of the patients showed 50% or greater increase of platelets as compared to pre-treatment levels. Moreover, 71% of the patients showed 50% or greater increase in reticulocyte count as compared to pre-treatment levels.

TABLE 14

|  | Evaluable | Responders | [Magnitude] |
|---|---|---|---|
| ANC ≧ 50%↑ | 17 | 5 (29%) | [330-105/μl] |
| ANC < 1000 | 8 | 3 (38.5%) |  |
| ANC > 1000 | 9 | 2 (22%) |  |
| Platelets ≧ 50%↑ | 9 | 3 (33%) | [23-32,000/μl] |
| >50,000/μl | 3 | 3 (100%) |  |
| <50,000/μl | 6 | 0 |  |
| Retic count ≧ 50%↑ | 14 | 10 (71%) | [0.4%-4.8%] |
| RBC Transfusion (≦50%↓) | 13 | 0 |  |
| BM Blasts ↑ (RAEB) | 5 | 2 (RAEB-t, AML) |  |

TABLE 14-continued

|  | Evaluable | Responders | [Magnitude] |
|---|---|---|---|
| Hemoglobin > 1.5 g/dl↑ | 7 | 1 |  |
| Ring Sideroblast | 7 | 3 ↓ [47%-100%] |  |

Bone marrow progenitor cells were recovered from the treated patients and assayed for their ability to form CFU-GEMM, BFU-E and CFU-GM colonies in standard methylcellulose assays. The results indicated that subcutaneous administration of amifostine in MDS patients was effective in inducing bone marrow cell growth.

9. EXAMPLE

Subcutaneous Administration of Amifostine and Radiation Therapy in Patients with Head and Neck Cancer

9.1 Subcutaneous Administration of Amifostine in Patients with Head and Neck Cancer The advantages of subcutaneous (sc) administered amifostine was demonstrated by comparing the results of a phase II trial of subcutaneously administered amifostine and radiation therapy in head and neck cancer patients with the results of a study wherein the patients received IV amifostine and radiation therapy for head and neck cancer (Brizel, *J Clin Oncol* 18:3339-3345, 2000).

In the phase II study all patients were undergoing radiation therapy for histologically confirmed squamous cell carcinoma of the head and neck region. Patients were allowed to enter the study following surgery with curative intent as soon as the wound has healed but no later than 12 weeks post operatively. Patients were at least 18 years of age with an expected survival rate of at least 12 months, a Karnofsky performance status of at least 70, no evidence of a distant metastatic disease, had a granulocyte count (segs and bands) of at least 2000/mm$^3$ and a platelet count of at least 100,000/mm$^3$, a serum creatinine of less than 2.0 mg/dL, a total bilirubin of less than 2.0 mg % and a SGOT of 3 times or less the upper limit of normal, had at least 75% of each parotid gland in the treatment fields that received a minimum dose of 40 Gy, and were not entered in any other investigational therapeutic trials.

Patients were excluded if they had a primary lesion of the parotid gland, would be receiving hyperfractionated or accelerated radiotherapy, had a history of prior malignancies within the past 5 years other than non-melanomatous skin cancers that had been controlled or carcinoma in situ of the cervix, were receiving concurrent chemotherapy (patients may have received chemotherapy for this head and neck cancer more than three weeks prior to enrollment), were concurrently using pilocarpine, had been treated with any investigational drugs more than 4 weeks prior to entering the study, had general or psychological conditions that would not permit the patient to complete the study, or were women of child bearing potential not using an effective method of birth control.

Patients received amifostine as two 250 mg subcutaneous injections (1.25 mL each) into two locations on the abdominal wall 60 minutes (±15 minutes) prior to radiation therapy (1.8-2.0 Gy/day for 25-35 fractions). Patients were hydrated with 250 cc of fluid orally 30 minutes prior to amifostine to assure that they were not dehydrated or have a decreased vascular volume. Patients were kept in a supine position during amifostine administration and for 10 minutes following amifostine administration. Blood pressure and pulse were obtained prior to subcutaneous administration and repeated 10 minutes following administration. An IV was available to treat hypotension if it occurred. Patients received full supportive care including antiemetics, antibiotics, transfusions of blood and blood products, and the like when needed. Prophylactic antiemetics were not administered. If patients experienced nausea and vomiting they were administered either prochlorperazine, 10 mg PO, 30 minutes prior to therapy, repeating every 4 to 6 hours following therapy as needed or ondansetron, 8 mg PO, 30 minutes prior to therapy, repeating every 4 hours following therapy as needed.

Radiation therapy was provided with linear accelerators with appropriate photon and electron boosting to the nodes or Cobalt 60. The appropriate photon energy was based on optimizing the radiation therapy dose distribution within the target volume and minimizing dose to normal tissue. Patients were reproducibly mobilized and radio-opaque markers were used to delineate the extent of nodal disease and, where possible, the primary tumor. All fields were treated once daily at 1.8-2.0 Gy per fraction, five days per week to a total dose of:

Post operative low risk patients: 50-60 Gy (primaries with negative tumor margins, node negative, node positive without extra capsular extension);

Post operative high risk patients: 60-66 Gy (positive tumor margins, N2, N3; any extra capsular extension in the neck); and Definitive radiation patients: 66-70 Gy.

Electrons were used to boost the nodal regions in the posterior neck when additional treatment to these regions was indicated. Fields were reduced to exclude the spinal cord at 40-46 Gy at the midplane. The entire neck, however, was irradiated to a minimum dose of 46 Gy (even at stage $N_o$) at anatomical levels of lymph node spread usually 2-4 cm below the skin surface. Positive neck nodes received a minimum dose of 60 Gy in 30-35 fractions in 6-7 weeks. To supplement the dose to the posterior neck and clinically positive nodes, boost techniques included additional electron beam ($\geq 6$ MeV) to the posterior neck, wedge pair or oblique fields. Initially, clinically negative posterior neck nodes received a minimum dose of 44-46 Gy at 3 cm depth.

9.2 Results

Xerostomia was graded in each subject according to the RTOG criteria. 55 patients were enrolled, with 54 evaluable for xerostomia. Results are shown in Table 15, along with similar results from a phase III trial in which 200 mg/m² of amifostine was administered as a 3 minute IV infusion 15 to 30 minutes before radiation therapy (1.8-2 Gy/day, 54-70 Gy total)(Brizel, *J Clin Oncol* 18:3339-3345, 2000).

TABLE 15

| | SC Amifostine | IV Amifostine + RT | RT | p-value |
|---|---|---|---|---|
| N | 54 | 148 | 153 | |
| $\geq$Grade 2 acute xerostomia Incidence | | | | |
| All patients | 56% | 51% | 78% | <0.0001 |
| Patients receiving $\geq$60 Gy RT | 49% | 51% | 78% | <0.0001 |
| Median time to onset | 40 days | 45 days | 30 days | 0.0001 |
| Median cumulative RT dose to onset | 50 Gy | 60 Gy | 42 Gy | 0.0001 |

Acute xerostomia, i.e., $\leq$grade 2 on the RTOG scale, was observed in patients administered subcutaneous amifostine at a comparable rate to those that were administered IV amifostine. There were, however, no reports of Grade 3 hypotension or Grade 3 nausea/vomiting following SC amifostine (3% and 7%, respectively, with IV). Grade 3 generalized cutaneous toxicity occurred in 13% of patients (3% with IV). The results of this study demonstrate that subcutaneous (SC) amifostine, similar to IV amifostine, protects against radiation-induced xerostomia but reduces or avoids side effects known to occur with IV amifostine The data shows that SC amifostine provides comparable protective effects against radiation-induced xerostomia and reduces the amifostine-related side effects of nausea, vomiting, and hypotension in head and neck cancer patients.

10. EXAMPLE

Extended Window of Mucosal Radioprotection of Intravenous or Subcutaneous Amifostine in Rats 10.1 Experimental Design A rat RT model was used to examine the protective effects of amifostine following IV as well as subcutaneous (SC) administration, and to investigate the length of time between amifostine administration and RT. In these experiments, rats were given 200 mg/kg (1200 mg/m²) of amifostine IV or SC, and their head and neck regions exposed to 15.3 Gy of gamma irradiation at various times following amifostine administration. For 10 days after treatment, the rats were weighed and the oral cavities of the rats were examined for signs of mucositis. Mucosal erythema and mucosal edema were scored according to 0-5 and 0-2 scales, respectively, with the scores added to indicate overall mucositis. 10.2 Results The results for IV amifostine after 10 days are summarized in Table 16.

| Group | Pretreatment interval (hr.) | Erythema | Edema | Overall Mucositis |
|---|---|---|---|---|
| RT | NA* | 2.0 | 1.4 | 3.4 |
| RT + amifostine | 0.5 | 0 | 0 | 0 |
| RT + amifostine | 2 | 0 | 0 | 0 |
| RT + amifostine | 4 | 0 | 0 | 0 |
| RT + amifostine | 8 | 2.8 | 1.2 | 4.0 |

*(NA = not applicable).

At 200 mg/kg (1200 mg/m²), SC administration of amifostine gave radioprotection comparable to IV administration up to 4 hours prior to radiation therapy.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entireties for all purposes.

What is claimed is:

1. A method of protecting against xerostomia or mucositis caused by radiation therapy comprising:
   subcutaneously administering to a subject in need thereof an effective amount of amifostine about 8 to about 12 hours before the subject is exposed to the radiation therapy.

2. The method of claim 1, wherein patient is a cancer patient.

3. The method of claim 2, wherein the cancer is head and neck cancer.

4. The method of claim 1, wherein the amount administered is at least about 500 mg.

5. The method of claim 4, wherein the amount administered is at least about 500 mg to 1500 mg.

6. The method of claim 1, wherein the amount is administered in one or more divided subcutaneous injections.

7. The method of claim 1, wherein amifostine is administered in the form of a pharmaceutical composition comprising amifostine and a pharmaceutically acceptable diluent.

8. The method of claim 7, wherein the diluent is normal saline.

9. The method of claim 1, wherein the subject is a human.

10. The method of claim 1, wherein the xerostomia is acute xerostomia.

11. The method of claim 1, wherein the xerostomia is late xerostomia.

12. The method of claim 1, wherein the mucositis is acute mucositis.

13. The method of claim 1, wherein the mucositis is late mucositis.

14. A method of protecting against xerostomia or mucositis caused by cancer chemotherapy comprising:
   subcutaneously administering to a subject in need thereof an effective amount of amifostine about 8 to about 12 hours before the subject is exposed to the chemotherapy.

15. The method of claim 14, wherein the amount administered is at least about 500 mg.

16. The method of claim 15, wherein the amount administered is at least about 500 mg to 1500 mg.

17. The method of claim 14, wherein the compound is administered in one or more divided subcutaneous injections.

18. The method of claim 14, wherein amifostine is administered in the form of a pharmaceutical composition comprising amifostine and a pharmaceutically acceptable diluent.

19. The method of claim 18, wherein the diluent is normal saline.

20. The method of claim 14, wherein the subject is a mammal.

21. The method of claim 20, wherein the mammal is a human.

22. The method of claim 14, wherein the xerostomia is acute xerostomia.

23. The method of claim 14, wherein the xerostomia is late xerostomia.

24. The method of claim 14, wherein the mucositis is acute mucositis.

25. The method of claim 14, wherein the mucositis is late mucositis.

26. The method of claim 14 further comprising:
   subcutaneously administering to a subject in need thereof an effective amount of amifostine about 8 to about 12 hours before the subject is exposed to the radiation therapy.

27. The method of claim 26, wherein the xerostomia is acute xerostomia.

28. The method of claim 26, wherein the xerostomia is late xerostomia.

29. The method of claim 26, wherein the mucositis is acute mucositis.

30. The method of claim 26, wherein the mucositis is late mucositis.

* * * * *